(12) United States Patent
Kuczynski et al.

(10) Patent No.: US 9,086,368 B2
(45) Date of Patent: Jul. 21, 2015

(54) NON-DESTRUCTIVE DETERMINATION OF THE MOISTURE CONTENT IN AN ELECTRONIC CIRCUIT BOARD USING COMPARISON OF CAPACITANCE MEASUREMENTS ACQUIRED FROM TEST COUPONS, AND DESIGN STRUCTURE/PROCESS THEREFOR

(75) Inventors: Joseph Kuczynski, Rochester, MN (US); Wayne J. Rothschild, Rochester, MN (US); Kevin A. Splittstoesser, Stewartville, MN (US)

(73) Assignee: International Business Machines Corporation, Armonk, NY (US)

( * ) Notice: Subject to any disclaimer, the term of this patent is extended or adjusted under 35 U.S.C. 154(b) by 753 days.

(21) Appl. No.: 13/033,801

(22) Filed: Feb. 24, 2011

(65) Prior Publication Data

US 2012/0217987 A1    Aug. 30, 2012

(51) Int. Cl.
*G01R 31/3187* (2006.01)
*G01R 31/08* (2006.01)
(Continued)

(52) U.S. Cl.
CPC .......... *G01N 27/223* (2013.01); *G01R 31/2817* (2013.01); *H05K 1/0268* (2013.01); *G01N 27/221* (2013.01); *G01N 27/225* (2013.01); *G01N 27/226* (2013.01); *G01N 33/246* (2013.01); *G01R 1/04* (2013.01); *G01R 1/0408* (2013.01); *G01R 27/26* (2013.01); *G01R 31/00* (2013.01); *G01R 31/2818* (2013.01); *G01R 31/2851* (2013.01); *G01R 31/2886* (2013.01);
(Continued)

(58) Field of Classification Search
CPC .... G01R 27/26; G01R 31/00; G01R 31/2887; G01R 31/2886; G01R 1/0408; G01R 1/04; G01R 31/2851; H05K 1/00; G01N 27/223; G01N 27/226; G01N 27/225; G01N 27/221; G01N 33/246
See application file for complete search history.

(56) References Cited

U.S. PATENT DOCUMENTS 4,057,823 A * 11/1977 Burkhardt et al. ............ 257/414
4,224,565 A *  9/1980 Sosniak et al. ................ 324/694
(Continued)

OTHER PUBLICATIONS

Fu et al., "iNEMI HFR-free Program Report", Aug. 2009, Electronic Packaging Technology & High Density Packaging, 2009. ICEPT-HDP '09. International Conference.*
(Continued)

*Primary Examiner* — Patrick Assouad
*Assistant Examiner* — Hoang X Nguyen
(74) *Attorney, Agent, or Firm* — Matthew J. Bussan

(57) ABSTRACT

Two test coupons are utilized in an apparatus, method and design process/structure for determining the moisture content in an electronic circuit board (e.g., a printed circuit board (PCB) or panel). The first coupon has a laminate stack-up with voltage planes separated from each other by dielectric material. These voltage planes include etched clearances with neither plated through holes (PTHs) nor drilled holes extending therethrough. The second coupon is substantially identical to the first coupon except that each of the voltage planes of the first coupon includes PTHs extending through etched clearances corresponding to the etched clearances of the first coupon. In one embodiment, an alarm indicating unacceptably high moisture content is generated if a delta capacitance calculated as a difference between capacitance measurements acquired from the respective coupons is greater than a threshold. Preferably, the alarm notifies a user that at least one aqueous process related to PTH formation is implicated.

25 Claims, 10 Drawing Sheets

(51) Int. Cl.

| | |
|---|---|
| *G01R 31/02* | (2006.01) |
| *G01R 31/304* | (2006.01) |
| *H05K 1/00* | (2006.01) |
| *H05K 7/00* | (2006.01) |
| *H05K 1/11* | (2006.01) |
| *G01N 27/22* | (2006.01) |
| *H05K 1/02* | (2006.01) |
| *G01R 1/04* | (2006.01) |
| *G01R 31/28* | (2006.01) |
| *G01R 31/00* | (2006.01) |
| *G01R 27/26* | (2006.01) |
| *G01N 33/24* | (2006.01) |
| *H05K 1/16* | (2006.01) |

(52) U.S. Cl.
CPC .............. *G01R 31/2887* (2013.01); *H05K 1/00* (2013.01); *H05K 1/162* (2013.01); *H05K 2203/162* (2013.01)

(56) References Cited

U.S. PATENT DOCUMENTS

| | | | | |
|---|---|---|---|---|
| 4,565,966 | A * | 1/1986 | Burr et al. .................... | 324/519 |
| 4,638,346 | A * | 1/1987 | Inami et al. .................. | 257/253 |
| 4,939,469 | A | 7/1990 | Ludwig et al. | |
| 5,345,821 | A | 9/1994 | Reich et al. | |
| 6,278,052 | B1 * | 8/2001 | Takehara et al. ............. | 136/244 |
| 6,333,633 | B1 | 12/2001 | Honjo et al. | |
| 6,498,381 | B2 * | 12/2002 | Halahan et al. .............. | 257/449 |
| 6,521,841 | B2 * | 2/2003 | Kawaguchi .................. | 174/250 |
| 6,756,793 | B2 * | 6/2004 | Hirono et al. ................ | 324/690 |
| 6,828,778 | B2 * | 12/2004 | Jacobsen et al. ......... | 324/754.07 |
| 6,904,789 | B2 | 6/2005 | Campbell et al. | |
| 7,032,448 | B2 * | 4/2006 | Hamamoto ............... | 73/335.04 |
| 7,129,732 | B1 | 10/2006 | Knadle | |
| 7,333,346 | B2 * | 2/2008 | Miyagawa et al. ........... | 361/784 |
| 7,340,952 | B2 * | 3/2008 | Tanida ..................... | 73/335.02 |
| 7,471,093 | B2 * | 12/2008 | Arisaka ...................... | 324/664 |
| 7,571,637 | B2 * | 8/2009 | Chen et al. ..................... | 73/73 |
| 7,676,920 | B2 * | 3/2010 | Farkas et al. .................. | 29/852 |
| 2002/0141136 | A1 * | 10/2002 | Toyoda et al. ................ | 361/302 |
| 2004/0108862 | A1 * | 6/2004 | Azuma et al. ................ | 324/691 |
| 2009/0107220 | A1 * | 4/2009 | Chen et al. .................... | 73/73 |
| 2010/0277197 | A1 * | 11/2010 | Deutsch et al. .............. | 324/758 |
| 2012/0052417 | A1 * | 3/2012 | Doyle et al. .................. | 430/5 |

OTHER PUBLICATIONS

Tisdale et al., "iNEMI BFR-Free PCB Materials Evaluation Project Report", Aug. 2008.*

Reid, "Dielectric Performance in Lead-Free Assembly", Mar. 2009, Printed Circuit Design & Fab, http://pcdandf.com/cms/magazine/220-2009-issues/5884-dielectric-performance-in-lead-fr.*

Tisdale et al., "iNEMI Halogen-Free Project Phase 2 Proposal", Mar. 2007, iNEMI, http://thor.inemi.org/webdownload/projects/ese/Halogen-Free/HF_Phase_2_March_22_07.pdf.*

Chris Hunt, Martin Wickham, Owen Thomas and Ling Zou, "Assessment of Moisture Content Measurement Methods for Printed Circuit Boards", APEX 2010.*

Davignon et al., "iNEMI HFR-Free Leadership Project Report", Oct. 20-22, 2010, IEEE, DOI 10.1109/IMPACT.2010.5699673, p. 1-7.*

Christopher Hunt, Owen Thomas, Martin Wickham, "Moisture Measurements in PCBs and Impact of Design on Desorption Behavior", Apr. 12-14, 2011, IPC APEX EXPO Technical Conference.*

Rothschild, Wayne, "Description of IBM PN 44V5528 (WIC20B)", International Business Machines Corporation, Armonk, New York, dated Apr. 10, 2009, pp. 1-13.

O'Toole et al., "Pb-Free Reflow, PCB Degradation and Moisture Absorption", DfR Solutions, College Park, Maryland, dated Jul. 16, 2009, pp. 1-13. (Available at http://www.ems007.com/pages/zone.cgi?a=51657&_pf_=1).

O'Toole et al., "Pb-Free Reflow, PCB Degradation, and the Influence of Moisture Absorption", DfR Solutions, College Park, Maryland, pp. 1-63, dated Feb. 20, 2009. (Available at http://www.dfrsolutions.com/uploads/publications/2009_02_Pb-Free.Degrade.MoisturePPT.pdf).

Smetana, et al., "Bare Board Material Performance after Pb-Free Reflow", IPC APEX EXPO, Las Vegas, Mar. 31-Apr. 2, 2009, pp. 1-37. (Available at http://www.circuitmart.com/pdf/bare_board_performance_after_reflow.pdf).

Knadle, Kevin, "Reliability and Failure Mechanisms of Laminate Substrates in a Pb-free World", dated Jul. 30, 2009, pp. 1-13. (Available at http://www.circuitmart.com/pdf/reliability_failure_mechanism_laminate.pdf).

"IPC APEX EXPO Technical Conference 2011", printed from <http://toc.proceedings.com/11628webtoc.pdf> on Oct. 29, 2014, 8 pages.

* cited by examiner

NON-DESTRUCTIVE DETERMINATION OF THE MOISTURE CONTENT IN AN ELECTRONIC CIRCUIT BOARD USING COMPARISON OF CAPACITANCE MEASUREMENTS ACQUIRED FROM TEST COUPONS, AND DESIGN STRUCTURE/PROCESS THEREFOR

BACKGROUND OF THE INVENTION

1. Field of Invention

The present invention relates in general to the field of testing electronic circuit boards. More particularly, the present invention relates to a method of determining the moisture content in an electronic circuit board (e.g., a printed circuit board, a panel that includes one or more printed circuit boards, or a special printed circuit board test panel) using two test coupons and a comparison of capacitance measurements acquired from the two coupons, and an apparatus, design process and design structure therefor.

2. Background Art

The structure of the laminate within module sites of printed circuit boards (PCBs) may be damaged when the PCBs are subjected to soldering operations. The likelihood that this damage will occur increases with increasing soldering temperatures and, as a result, reliability risks for the PCBs increase as well. Plated through holes (PTHs) in the PCB, especially PTHs within module sites, are particularly vulnerable to this failure mechanism. Higher soldering temperatures are a consequence of compliance with the Restriction of Hazardous Substances Directive or RoHS. Under RoHS, eutectic tin/lead solder is replaced by lead-free solders (e.g., Sn—Ag—Cu solder) with higher melting temperatures.

A key factor in this failure mechanism is the rapid volatilization (during soldering) of water that is entrapped within the laminate during fabrication of the PCB. Specifically, water may be entrapped during aqueous processes that occur after the PCB is drilled and up to the early phases of plating of the drilled holes (to form PTHs). For a given PCB design and laminate material, the amount of water that is entrapped will vary (up to a point) with the details of some aspects of the fabrication process. Similarly, the effects of entrapped water upon the structural integrity of the laminate within a given PCB will vary with the PCB design, the laminate material, and some aspects of the fabrication process. It is important that a PCB fabricator take steps to minimize the amount of entrapped water within a given PCB. Unfortunately, direct measurements of water content (especially within module sites) are not practical.

Typically, direct measurement of the water content in a PCB, especially within module sites, is performed through a destructive testing technique. For example, the water content in a PCB may be determined by Karl Fischer (KF) titration, which requires the sample to be ground to a fine powder and then subjected to coulometric analysis.

It is also known to indirectly measure the water content in a PCB through capacitance. This concept is based upon the fact that the capacitance of a given laminate increases with increasing water content. Such a scheme is disclosed in U.S. Pat. No. 7,571,637 B2, issued Aug. 11, 2009 to Chen et al., entitled "DESIGN STRUCTURE FOR AN ON-CHIP REAL-TIME MOISTURE SENSOR FOR AND METHOD OF DETECTING MOISTURE INGRESS IN AN INTEGRATED CIRCUIT CHIP", assigned to the same assignee as the present application. In the Chen et al. patent, an integrated circuit (IC) chip includes one or more moisture-sensing units and a moisture monitor. The moisture monitor can be configured to provide a real-time moisture detected-signal for signaling that moisture ingress into the integrated circuit chip has occurred by comparing the sense signals of the moisture-sensing units (e.g., the voltage on a voltage node Vc across a metal-insulator-metal (MIM) capacitor) to a threshold voltage. While the design structure disclosed in the Chen et al. patent may be effective for monitoring ingress of moisture into an integrated chip during the operational lifetime of the chip, the design structure does not address monitoring the ingress of moisture during fabrication of the integrated chip.

Another scheme for indirectly measuring moisture content in a PCB using capacitance is disclosed in an article by O'Toole et al., entitled "Pb-Free Reflow, PCB Degradation and Moisture Absorption", published by DfR Solutions, College Park, Md., dated Jul. 16, 2009. In the O'Toole et al. article, two coupon designs were utilized to investigate the effect of Pb-free solder reflow on the degradation of PCBs. Each coupon contained three sections (i.e., Sections 1, 2 and 3) and a total of six test structures (i.e., Test Structures A, B, C, D, E and F) were incorporated into the design. The three sections of the PCB all consisted of the basic shield-over-shield copper plane design; however, they differed in their content of PTHs and non-functional pads. Section 1 of each coupon, which included Test Structure A, contained only copper planes without PTHs. Section 1 resulted in the largest shield-over-shield capacitance measurements and facilitated observation of clear trends for this data. Section 2 of each coupon, which included Test Structures B and C, contained copper planes, PTHs and nonfunctional pads on every layer. Section 2 allowed capacitance measurements to be made for both shield-over-shield and PTH-shield trends on the same coupon. Section 3 of each coupon, which included Test Structures D, E and F, contained copper planes, PTHs and non-functional pads on every other layer. In reflow simulation, Test Structures B and C showed much greater change in shield-over-shield capacitance measurements compared to Test Structure A.

The scheme disclosed in the O'Toole article has a number of disadvantages. Unfortunately, because Test Structure A contained only copper planes without PTHs, the clearances etched in the copper planes (sometimes referred to as a "swiss-cheese" pattern or "anti-pads") for the PTHs were omitted along with the PTHs. The omission of the etched clearances from Test Structure A diminishes the usefulness of the comparison of the shield-over-shield capacitance measurements between Test Structure A and Test Structures B and C. In essence, this is an "apples and oranges" comparison because the area of copper planes without the etched clearances is larger than the area of the copper planes with the etched clearances—this is why the Section 1 resulted in the largest shield-over-shield capacitance measurements. Moreover, for each test structure disclosed in the O'Toole article, alternating planes of the PCB stack-up (i.e., the PCB stack-up consists of 26 layers of copper foil with dielectric between each layer) are tied to two different nodes (i.e., nodes A1 and A2 for Test Structure A, nodes B1 and B2 for Test Structure B, nodes C1 and C2 for Test Structure C). This arrangement does not facilitate capacitance measurements between individual planes of the PCB stack-up and, hence, it is not possible to measure water content in a particular area of the PCB stack-up. Finally, the scheme disclosed in the O'Toole article requires coupons taken from production panels to be exposed to reflow simulation—a costly and time-consuming step.

Therefore, a need exists for an enhanced mechanism for the non-destructive determination of the moisture content in an electronic circuit board (e.g., a PCB, a panel that includes one or more PCBs, or a special PCB test panel) using test coupons during fabrication.

SUMMARY OF THE INVENTION

According to the preferred embodiments of the present invention, an apparatus, method, design process, and design structure for determining the moisture content in an electronic circuit board (e.g., a printed circuit board (PCB), a panel that includes one or more PCBs, or a special PCB test panel) employ one or more coupon sets, each set having two test coupons. The first coupon has a laminate stack-up with voltage planes separated from each other by dielectric material. These voltage planes include etched clearances with neither plated through holes (PTHs) nor drilled holes extending therethrough. The second coupon is substantially identical to the first coupon except that each of the voltage planes of the second coupon includes PTHs extending through etched clearances corresponding to the etched clearances of the first coupon.

One or more coupon sets in accordance with the preferred embodiments of the present invention, provides a quick, non-destructive, semi-quantitative means of accessing the effects of process changes or process variability upon water content in the laminate of a production part (e.g., a PCB or a panel). The present invention, which takes advantage of the fact that the capacitance of a given laminate increases with increasing water content, may be used as a moisture management tool. Moisture management is desirable to reduce the propensity for laminate damage that may occur as the result of exposure of a PCB to higher soldering temperatures.

In one embodiment, an alarm indicating unacceptably high moisture content is generated if a delta capacitance calculated as a difference between capacitance measurements acquired from the respective coupons is greater than a threshold. Preferably, the alarm notifies a user that at least one aqueous process related to PTH formation is implicated. An alarm indicating unacceptably high moisture content is also generated if a capacitance measurement acquired from the first coupon without PTHs is greater than a threshold. Preferably, this alarm notifies the user that a raw laminate used to fabricate the first coupon without PTHs had unacceptably high moisture content "as delivered" and/or a clearance etch process used to produce the etched clearances in the raw laminate is/are implicated in the unacceptably high moisture content.

BRIEF DESCRIPTION OF THE DRAWINGS

The preferred exemplary embodiments of the present invention will hereinafter be described in conjunction with the appended drawings, where like designations denote like elements.

DETAILED DESCRIPTION OF THE PREFERRED EMBODIMENTS

1. Overview

Figure 1:
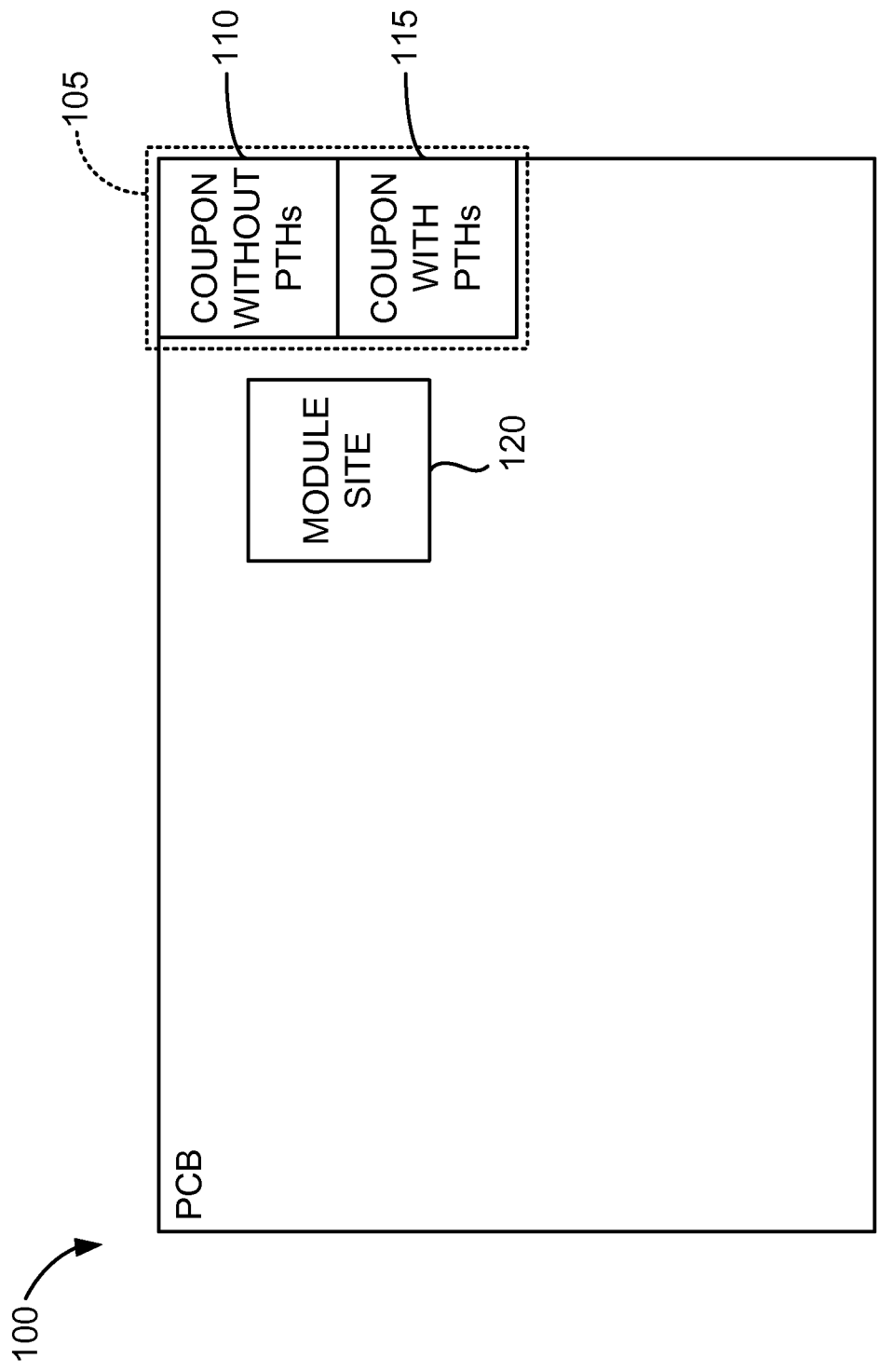
FIG. 1 is a block diagram illustrating a printed circuit board (PCB) incorporating a set of two coupons, i.e., one coupon without plated through holes (PTHs) and one coupon with PTHs in accordance with an embodiment of the present invention.

According to the preferred embodiments of the present invention, an apparatus, method, design process, and design structure for determining the moisture content in an electronic circuit board (e.g., a printed circuit board (PCB), a panel that includes one or more PCBs, or a special PCB test panel) employ one or more coupon sets, each set having two test coupons. The first coupon has a laminate stack-up with voltage planes separated from each other by dielectric material. These voltage planes include etched clearances with neither plated through holes (PTHs) nor drilled holes extending therethrough. The second coupon is substantially identical to the first coupon except that each of the voltage planes of the second coupon includes PTHs extending through etched clearances corresponding to the etched clearances of the first coupon.

One or more coupon sets in accordance with the preferred embodiments of the present invention, provides a quick, non-destructive, semi-quantitative means of accessing the effects of process changes or process variability upon water content in the laminate of a production part (e.g., a PCB or a panel). The present invention, which takes advantage of the fact that the capacitance of a given laminate increases with increasing water content, may be used as a moisture management tool. Moisture management is desirable to reduce the propensity for laminate damage that may occur as the result of exposure of a PCB to higher soldering temperatures.

In one embodiment, an alarm indicating unacceptably high moisture content is generated if a delta capacitance calculated as a difference between capacitance measurements acquired from the respective coupons is greater than a threshold. Preferably, the alarm notifies a user that at least one aqueous process related to PTH formation is implicated. An alarm indicating unacceptably high moisture content is also generated if a capacitance measurement acquired from the first coupon without PTHs is greater than a threshold. Preferably, this alarm notifies the user that a raw laminate used to fabricate the first coupon without PTHs had unacceptably high moisture content "as delivered" and/or a clearance etch process used to produce the etched clearances in the raw laminate is/are implicated in the unacceptably high moisture content.

2. Detailed Description

In accordance with the preferred embodiments of the present invention, a set of at least two test coupons, i.e., at least one test coupon with plated through holes (PTHs) and at least one test coupon without PTHs, is incorporated into an electronic circuit board. Suitable electronic circuit boards into which the set of test coupons may be incorporated include, but are not limited to, a printed circuit board (an exemplary embodiment is described below with reference to FIG. 1), a panel that also incorporates one or more printed circuit boards (an exemplary embodiment is described below with reference to FIG. 2), or a special printed circuit board test panel (an exemplary embodiment is described below with reference to FIG. 3). One skilled in the art will appreciate, however, that the set of test coupons may be incorporated into other electronic circuit boards such as flex circuits, backplanes, backpanels, organic chip carriers, and the like.

For each capacitance measurement region within the laminate stack-up of the coupons, capacitances are measured and compared between the test coupon without PTHs and the test coupon with PTHs. Typically, the measured capacitance of the test coupon with PTHs will be higher than that of the test coupon without PTHs. This capacitance difference can be attributed to water that is entrapped within the laminate between the PTHs during aqueous processes that occur between when the laminate is drilled and partially into the PTH plating process. Changes in the capacitance difference can be attributed to changes in the amount of water entrapped in the laminate between PTHs.

The test coupon without PTHs and the test coupon with PTHs are, in essence, akin to a control sample and an experimental sample, respectively, in a controlled experiment. In a controlled experiment, the effect of an independent variable is tested by comparing the results obtained from an experimental sample against a control sample, which is nearly identical to the experimental sample except for the independent variable. In accordance with the preferred embodiments of the present invention, the test coupons with and without PTHs are substantially identical to each other except for the independent variable, which is the presence of the PTHs (along with various structural features associated with the PTHs, such as drilled holes, as well as various processes used to form the PTHs).

Typically, it is desirable in a controlled experiment for the control sample to be as near as possible to being identical to the experimental sample. As a consequence, in accordance with the preferred embodiments of the present invention, the test coupon without PTHs has etched clearances (described below with reference to FIG. 6) in voltage planes used for capacitance measurement just like the corresponding etched clearances (described below with reference to FIG. 7) in corresponding voltage planes in the test coupon with PTHs. Otherwise, the capacitance measurements obtained from the test coupon without PTHs would be skewed relative to the capacitance measurements obtained from the test coupon with PTHs (i.e., the capacitance measured between the voltage planes would be greater if the etched clearances were omitted from the test coupon without PTHs because the capacitance increases with plane area). Similarly, for the test coupon with PTHs, it is critical that the web within the array on the voltage planes be manufactured as defined, at least with normal manufacturing tolerances (e.g., there shall be no breaks in "swiss cheese" between the vias on the voltage planes, which is a solution manufacturers have been known to employ against etched clearance/drilled hole registration problems).

In the test coupon without PTHs and the test coupon with PTHs, the voltage planes used for capacitance measurements are separated from each other by a dielectric material. Layers in addition to the dielectric material may separate the voltage planes. Also, each of the test coupons typically includes more than a single pair of voltage planes from which capacitance measurements may be acquired. The voltage planes used for capacitance measurements are identically located in the laminate stack-up (an exemplary stack-up is described below with reference to FIG. 5) of the test coupons. Typically, the laminate stack-up of the test coupons substantially replicates the laminate stack-up of the electronic circuit board. In addition, as discussed in more detail below, the test coupons replicate selected design features of the electronic circuit board, i.e., at least one design feature of the electronic circuit board that is known or predicted to be associated with solder reflow-induced damage to the laminate of the electronic circuit board. Such design features include, but are not limited to, via-to-via pitch, drilled via diameter, drilled via clearance diameter, array size, and the like.

FIG. 1 is a block diagram illustrating a printed circuit board (PCB) 100 that incorporates a set 105 of two coupons, i.e., one coupon 110 without plated through holes (PTHs) and one coupon 115 with PTHs in accordance with an embodiment of the present invention. The coupon 110 without PTHs and the coupon 115 with PTHs are substantially identical but for the absence and presence, respectively, of PTHs and drilled holes through the laminate stack-up (an exemplary layout and an exemplary stack-up of these coupons are described below with reference to FIG. 4 and FIG. 5, respectively).

Typically, the coupons 105 and 110 replicate the laminate stack-up and selected design features of the PCB 100. The coupons 105 and 110 preferably include one or more design features that reflect at least one feature of the PCB 100 that is known or predicted to be associated with solder reflow-induced damage to the laminate of the PCB 110 within or near the at least one PCB feature. Such design features include, without limitation, via-to-via pitch, drilled via diameter, drilled via clearance diameter, array size, and the like. Typically, the aforementioned PCB feature(s) is/are within or near one or more module sites on the PCB 110 (e.g., a module site 120).

The coupons 105 and 110 are preferably removable from the PCB 100. For example, the PCB 100 may be scored to facilitate removal of the coupons 105 and 110 from the PCB 100. However, scoring is but one technique known in the art to facilitate removal of test coupons from a PCB. One skilled in the art will appreciate that any other technique known in the art may be used to facilitate removal of the coupons 105 and 110 from the PCB 100.

The moisture content of the PCB 100 may be determined using the apparatus illustrated in FIG. 1. Preferably, as discussed below with reference to the method illustrated in FIG. 8, the coupons 105 and 110 are removed from the PCB 100 and the moisture content of the PCB 100 determined before the PCB 100 is subjected to reflow conditions.

Preferably, as illustrated in FIG. 1, the coupons 105 and 110 are located adjacent to each other. By locating the coupons 110 and 115 adjacent to one another, each coupon is exposed to substantially the same conditions during fabrication of the PCB 100. Typically, it is desirable in a controlled experiment to expose a control sample to the same conditions as an experimental sample. Accordingly, but for the presence of the PTHs (along with various structural features associated with the PTHs, such as drilled holes, as well as various processes used to form the PTHs), the coupons 110 and 115 would likely have the same moisture content as each other.

One skilled in the art will appreciate, however, that the coupons 110 and 115 may be located anywhere with respect to one another on the PCB 100.

Typically, it is desirable to locate the coupons 110 and 115 near a module site 120 on the PCB 100 that is known or predicted to be associated with solder reflow-induced damage to the laminate of the PCB 100. By locating the coupons 110 and 115 near the module site 120, the coupons and the module site are exposed to substantially the same conditions during fabrication of the PCB 100. Accordingly, at least the coupon 115 with PTHs will likely have the same moisture content as the module site 120. The coupon 110 without PTHs, on the other hand, may have lower moisture content than either the coupon 115 with PTHs or the module site 120, owing to the omission of PTHs in the coupon 110.

By locating the coupons 110 and 115 near the module site 120 as illustrated in FIG. 1, it is possible in accordance with the preferred embodiments of the present invention to indirectly quantify the effects of changes in fabrication processes upon water content within the module site 120 (e.g., optimize fabrication processes based on water content) or variations in the water content in the module site 120 due to process variations for a given design of the PCB 100, using a given laminate material (e.g., monitor the water content in production PCBs for variations due to process variations).

One skilled in the art will appreciate, however, that the coupons 110 and 115 may be located anywhere in the PCB 100 and need not be located near the module site 120.

Moreover, it may be desirable to provide the PCB 100 with more than a single coupon set 105. For example, it may be desirable to provide a plurality of coupon sets 105 at different locations on the PCB 100 so that each coupon set 105 may experience different conditions during fabrication of the PCB 100. Likewise, it may be desirable to locate a plurality of coupon sets 105, respectively, near a plurality of module sites on the PCB 100 that are known or predicted to be associated with solder reflow-induced damage to the laminate of the PCB 100.

Figure 2:
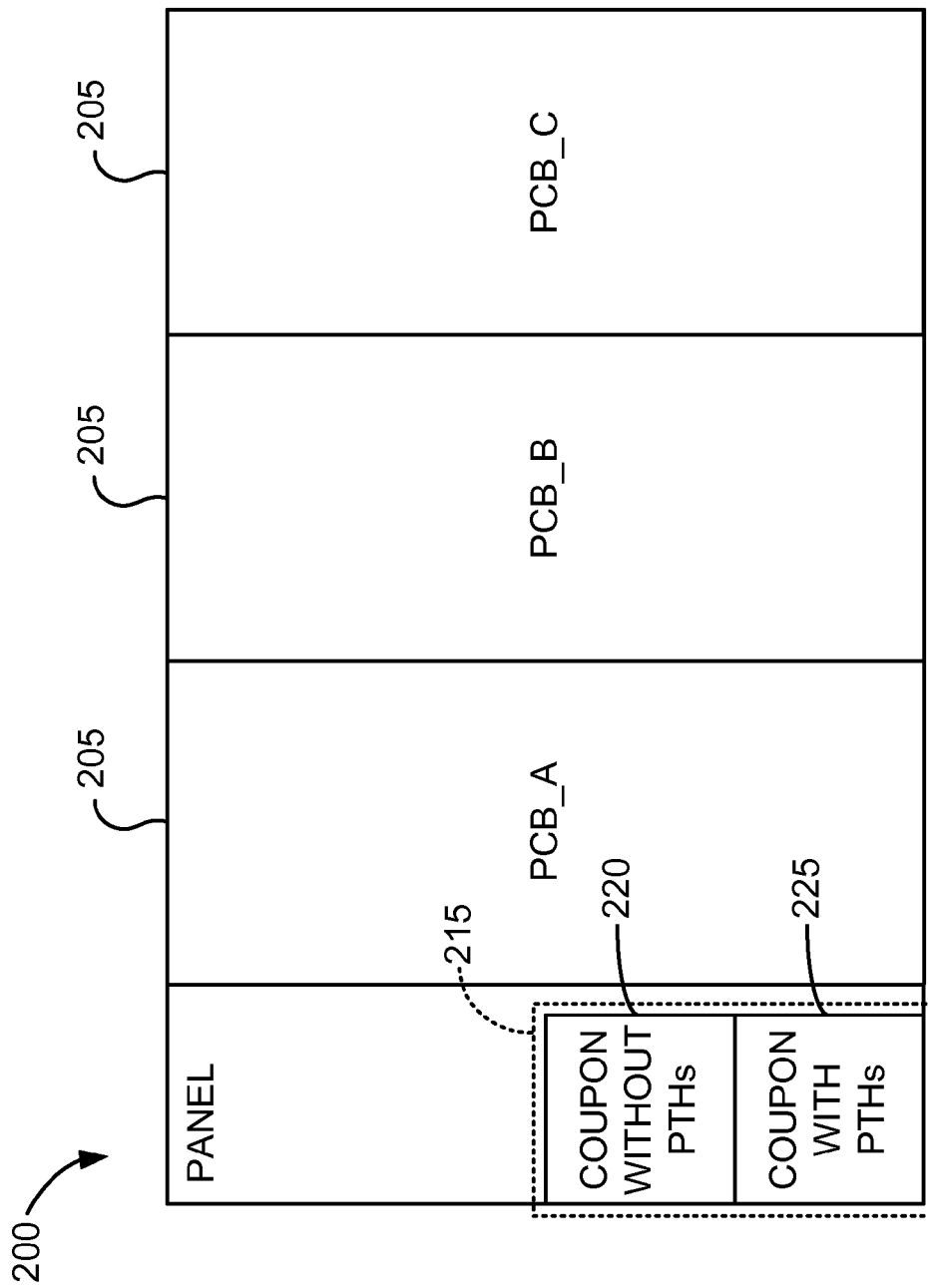
FIG. 2 is a block diagram illustrating a panel incorporating one or more printed circuit boards (PCBs) and a set of two coupons, i.e., one coupon without plated through holes (PTHs) and one coupon with PTHs in accordance with another embodiment of the present invention.

FIG. 2 is a block diagram illustrating a panel 200 incorporating one or more printed circuit boards (PCBs) 205 and set 215 of two coupons, i.e., one coupon 220 without plated through holes (PTHs) and one coupon 225 with PTHs in accordance with another embodiment of the present invention. The coupon 220 without PTHs and the coupon 225 with PTHs are substantially identical but for the absence and presence, respectively, of PTHs and drilled holes through the laminate stack-up (an exemplary layout and an exemplary stack-up of these coupons are described below with reference to FIG. 4 and FIG. 5, respectively).

Typically, as illustrated in FIG. 2, the PCBs 205 and the coupon set 215 are accommodated in separate areas of the panel 200. The PCBs 205 and the coupons 220 and 225 are preferably removable from the panel 200. For example, the panel 200 may be scored to facilitate removal of the PCBs 205 and the coupons 220 and 225 from the panel 200. However, scoring is but one technique known in the art to facilitate removal of PCBs and test coupons from a panel. One skilled in the art will appreciate that any other technique known in the art may be used to facilitate removal of the PCBs 205 and the coupons 220 and 225 from the panel 200.

The moisture content of a plurality of PCBs 205 that are simultaneously fabricated in separate areas of the panel 200 may be determined using the apparatus illustrated in FIG. 2 (i.e., the panel 200). Preferably, as discussed below with reference to the method illustrated in FIG. 8, the coupons 220 and 225 are removed from the panel 200 and the moisture content of the panel 200 determined before the panel 200 is subjected to reflow conditions.

Typically, the coupons 220 and 225 replicate the laminate stack-up and selected design features of the PCBs 205. The coupons 220 and 225 preferably include one or more design features that reflect at least one feature of the PCBs 205 that is known or predicted to be associated with solder reflow-induced damage to the laminate of the PCBs 205 within or near the at least one PCB feature. Such design features include, without limitation, via-to-via pitch, drilled via diameter, drilled via clearance diameter, array size, and the like. Typically, the aforementioned PCB feature(s) is/are within or near one or more module sites on the PCBs 205 (e.g., the module site 120 in FIG. 1).

Preferably, as illustrated in FIG. 2, the coupons 220 and 225 are located adjacent to each other. By locating the coupons 220 and 225 adjacent to one another, each coupon is exposed to substantially the same conditions during fabrication of the panel 200. Typically, it is desirable in a controlled experiment to expose a control sample to the same conditions as an experimental sample. Accordingly, but for the presence of the PTHs (along with various structural features associated with the PTHs, such as drilled holes, as well as various processes used to form the PTHs), the coupons 220 and 225 would likely have the same moisture content as each other.

One skilled in the art will appreciate, however, that the coupons 220 and 225 may be located anywhere with respect to one another on the panel 200.

Moreover, it may be desirable to provide the panel 200 with more than a single coupon set 215. For example, it may be desirable to provide a plurality of coupon sets 215 at different locations on the panel 200 so that each coupon set 215 may experience different conditions during fabrication of the panel 200. Likewise, it may be desirable to locate a coupon set 215 near each of the PCBs 205 and/or near a module site on the PCBs 205 known or predicted to be associated with solder reflow-induced damage to the laminate of the PCBs 205.

By locating a coupon set 215 near each of the PCBs 205 and/or near a module site on the PCBs 205, it is possible in accordance with the preferred embodiments of the present invention to indirectly quantify the effects of changes in fabrication processes upon water content within the PCB and/or module site (e.g., optimize fabrication processes based on water content) or variations in the water content in the PCB and/or module site due to process variations for a given PCB design, using a given laminate material (e.g., monitor the water content in production PCBs for variations due to process variations).

Figure 3:
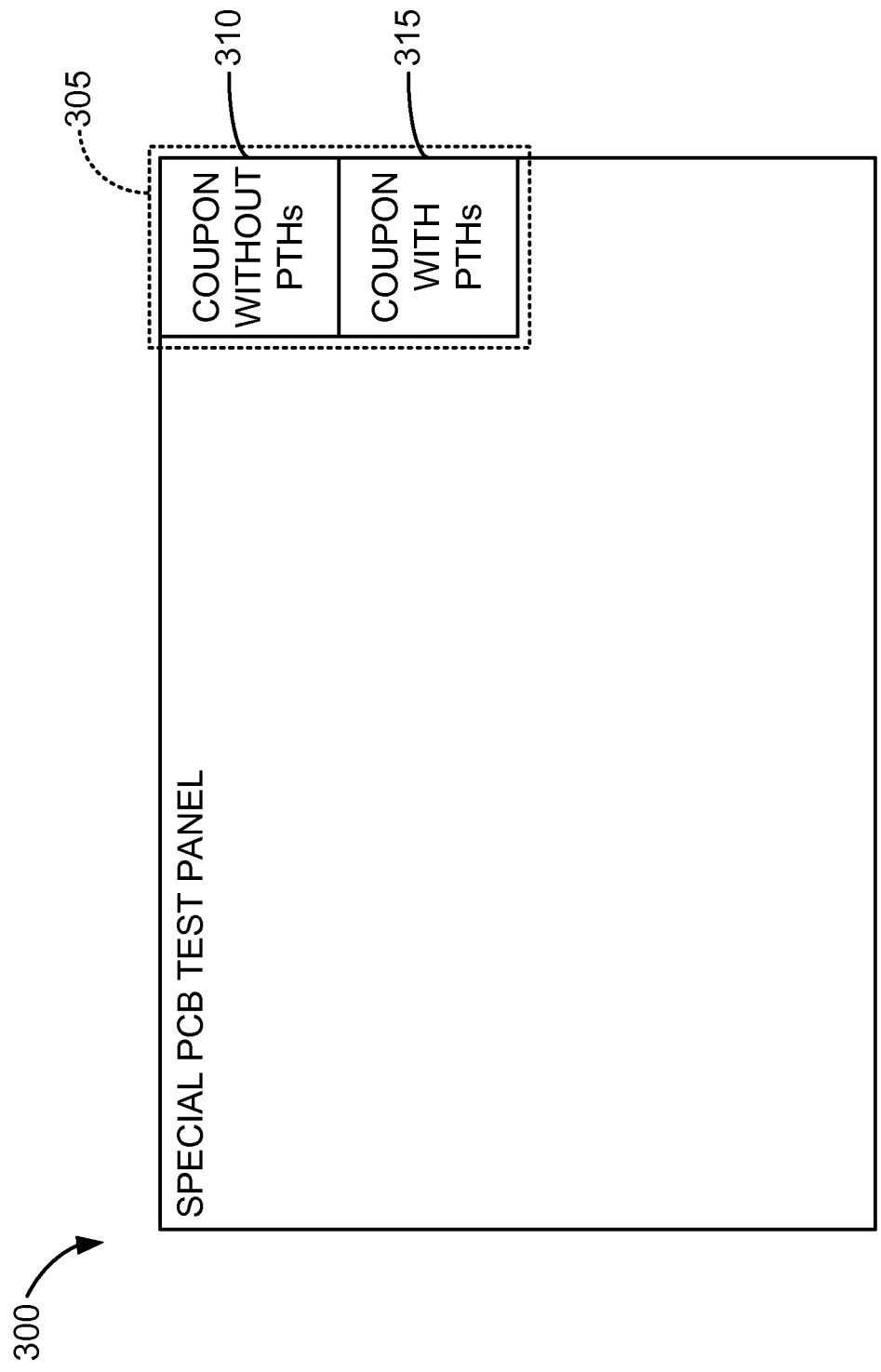
FIG. 3 is a block diagram illustrating a special printed circuit board (PCB) test panel incorporating a set of two coupons, i.e., one coupon without plated through holes (PTHs) and one coupon with PTHs in accordance with yet another embodiment of the present invention.

FIG. 3 is a block diagram illustrating a special printed circuit board (PCB) test panel 300 incorporating a set 305 of two coupons, i.e., one coupon 310 without plated through holes (PTHs) and one coupon 315 with PTHs in accordance with yet another embodiment of the present invention. The coupon 310 without PTHs and the coupon 315 with PTHs are substantially identical but for the absence and presence, respectively, of PTHs and drilled holes through the laminate stack-up (an exemplary layout and an exemplary stack-up of these coupons are described below with reference to FIG. 4 and FIG. 5, respectively).

Typically, the special PCB test panel 300 accommodates a plurality of coupon sets 305 (only one set is shown in FIG. 3). For example, the respective coupon sets 305 at different locations on the special PCB test panel 300 may include coupons built with varying moisture content to obtain pass/fail criteria data (e.g., discussed below with reference to FIG. 9). Likewise, it may be desirable to provide a plurality of coupon sets 305 at different locations on the special PCB test panel 300 so that each coupon set 305 may experience different conditions during fabrication of the special PCB test panel 300.

The coupons 310 and 315 in each coupon set 305 are preferably removable from the special PCB test panel 300. For example, the special PCB test panel 300 may be scored to facilitate removal of the coupons 310 and 315 from the special PCB test panel 300. However, scoring is but one technique known in the art to facilitate removal of test coupons from a panel. One skilled in the art will appreciate that any other technique known in the art may be used to facilitate removal of the coupons 310 and 315 from the special PCB test panel 300.

Typically, the coupons 310 and 315 replicate the laminate stack-up and selected design features of a production PCB (not shown in FIG. 3). The coupons 310 and 315 preferably include one or more design features that reflect at least one feature of the production PCB that is known or predicted to be associated with solder reflow-induced damage to the laminate of the production PCB within or near the at least one production PCB feature. Such design features include, without limitation, via-to-via pitch, drilled via diameter, drilled via clearance diameter, array size, and the like. Typically, the aforementioned production PCB feature(s) is/are within or near one or more module sites on the production PCBs (e.g., the module site 120 in FIG. 1).

Preferably, as illustrated in FIG. 2, the coupons 310 and 315 are located adjacent to each other. By locating the coupons 310 and 315 adjacent to one another, each coupon is exposed to substantially the same conditions during fabrication of the special PCB test panel 300. Typically, it is desirable in a controlled experiment to expose a control sample to the same conditions as an experimental sample. Accordingly, but for the presence of the PTHs (along with various structural features associated with the PTHs, such as drilled holes, as well as various processes used to form the PTHs), the coupons 310 and 315 would likely have the same moisture content as each other.

One skilled in the art will appreciate, however, that the coupons 310 and 315 may be located anywhere with respect to one another on the special PCB test panel 300.

Figure 4:
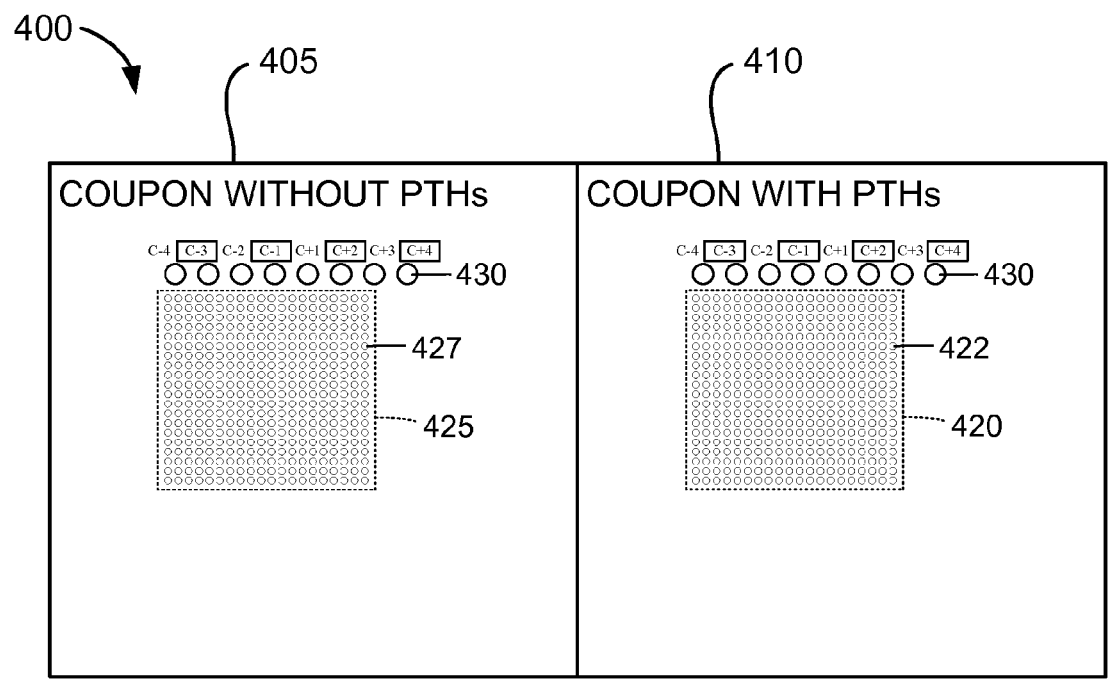
FIG. 4 is an enlarged top surface view illustrating an exemplary layout of the two coupons shown in FIG. 1-3.

FIG. 4 is an enlarged top surface view illustrating an exemplary layout 400 of the two coupons shown in FIG. 1-3. As illustrated in FIG. 4, a set of coupons includes a coupon 405 without PTHs (corresponding to coupons 110, 220 and 310 in FIGS. 1-3, respectively) and a coupon 410 with PTHs (corresponding to coupons 115, 225 and 315 in FIGS. 1-3, respectively). The coupons 405 and 410 are identical in size and, as discussed below, include an equal number of clearances. The particular layout of the coupons 405 and 410 illustrated in FIG. 4 is merely one example of a suitable coupon layout and is not intended to limit the present invention. One skilled in the art will appreciate that any suitable coupon layout may be used in accordance with the preferred embodiments of the present invention in lieu of the exemplary coupon layout 400 illustrated in FIG. 4.

As illustrated in FIG. 4, the coupons 405 and 410 each include a 20×20 array. One skilled in the art will appreciate, however, that the coupons 405 and 410 may include any size array. The coupon 410 with PTHs includes a 20×20 array 420 of vias (e.g., 8-mil vias) and clearances 422 (e.g., 26-mil clearances) on a predetermined pitch grid (e.g., 0.8-mm pitch grid). These vias and clearances 422 are better illustrated in FIG. 7, which shows them in the context of a voltage plane layer. The coupon 405 without PTHs, includes a 20×20 array 425 of clearances 427 (e.g., 26-mil clearances) on the predetermined pitch grid (e.g., 0.8-mm pitch grid). These clearances 427 are better illustrated in FIG. 6, which shows them in the context of a voltage plane layer. The clearances 427 have the same diameter and are on the same predetermined pitch grid as the clearances 422. The array 425 of the coupon 405 without PTHs is identical to the array 420 of the coupon 410 with PTHs except for omission of the vias (and the drilled holes for the vias) present in the array 420 of the coupon 410 with PTHs.

As also illustrated in FIG. 4, the coupons 405 and 410 each include 8 PTHs 430 (e.g., 40-mil PTH diameter) for measuring capacitance. The PTHs 430 for measuring capacitance are labeled "C−4", "C−3", "C−2", "C−1", "C+1", "C+2", "C+3", and "C+4" in FIG. 4, as denoted by markings immediately adjacent to the corresponding PTHs 430 on the top surface of the coupons. The PTHs 430 for measuring capacitance are located above the 20×20 array, with a PTH-to-PTH spacing of 100 mils to accommodate probes for capacitance measurement. One skilled in the art will appreciate that the coupons 405 and 410 may include any number of such PTHs for measuring capacitance. Each marking is a code (e.g., "C+1") that refers to the specific layer to which the immediately adjacent PTH 430 for measuring capacitance is uniquely connected. Typically, a translation table is used to translate the code to the actual layer number of the specific layer used. Alternatively, each marking may refer directly to the actual layer number of the specific layer to which the immediately adjacent PTH 430 is connected.

The PTHs 430 for measuring capacitance are connected to selected internal layers within the coupons 405 and 410 to allow dielectric capacitance measurements (up to 7 dielectric layers). An exemplary laminate stack-up of the coupons 405 and 410 is described below with reference to FIG. 5, including the selected internal layers to which the PTHs 430 for measuring capacitance are connected.

The exemplary layout 400 of the coupons 405 and 410 illustrated in FIG. 4 is based on the IBM Part Number 44V5528 (WIC20B) printed circuit board test vehicle design package, available from International Business Machines Corporation, Armonk, N.Y., that was developed primarily to allow indirect assessments of bulk and localized water content within the laminate within a 20×20 array of 8-mil vias on a 0.8-mm pitch grid. The WIC20B design also allows assessments of the effects of environmental stresses upon the structure and/or chemistry of the laminate used in its construction.

Although the WIC20B design package is conventional, its use in a set of coupons that includes one coupon without PTHs and one coupon with PTHs for comparison of capacitance measurements is new. A brief description of the WIC20B design package is presented below in order to provide a foundation from which to describe concepts of the present invention. Greater detail about the WIC20B design package is set forth in the document, W. Rothschild, "Description of IBM PN 44V5528 (WIC20B)", International Business Machines Corporation, Armonk, N.Y., pages 1-13, Apr. 10, 2009, which is hereby incorporated herein by reference in its entirety.

The WIC20B design package includes several features that are not pertinent to the present invention. Such features include PTHs for measuring inductance, traces used in inductance measurement, and a material characterization coupon for material characterization and other studies. These non-pertinent features of the WIC20B design package are not further described herein.

There is no established lay-up or overall thickness for the WIC20B design. Rather, the WIC20B design package consists of 2 external signal planes, 18 internal signal planes, and 26 voltage planes, as well as 3 solder mask layers (including none) for each external surface. A wide variety of different lay-ups (and, thus, a wide range of overall thicknesses) may be constructed by selecting layers from the WIC20B design package in accordance with a set of guidelines that are presented in the WIC20B design document. The WIC20B design package also allows for selection among different diameters of the clearance around the 8-mil vias. This WIC20B design defines the pitch (0.8-mm) and allows a range of drill sizes and clearances around those drilled holes on the voltage planes. The WIC20B design also includes the option of inclusion of unused lands on any signal plane, as well as choices of clearance diameters for each solder mask layer.

WIC is an acronym that describes the measurements that the WIC20B design package was designed to accommodate—W(eight), I(mpedance) and C(apacitance). The small size of the test coupon facilitates high precision gravimetric (weight) analyses. Most internal layers are wired to allow dielectric capacitance measurements (up to 7 dielectric layers) when following the guidelines that are provided in the WIC20B design document. Changes in these parameters may occur upon exposure of the test coupon to environmental stresses, such as solder reflow simulation or storage at ambient condition or at high temperature and/or high relative humidity. These changes may be indicative of changes in the composition of the laminate within the area array. Changes include migration of water, creation of air pockets (e.g., due to the creation of laminate cracks), and changes in resin chemistry (e.g., due to oxidation). Note that some of these changes might be detected electrically but not gravimetrically.

In the WIC20B design, a voltage divider on each voltage plane layer separates the 20×20 array and the PTHs used to measure capacitance from the remainder of the voltage plane. In accordance with the preferred embodiments of the present invention, a voltage divider (not shown in FIG. 4) on each voltage plane is provided between the coupons 405 and 410.

Also in the WIC20B design, pairs of voltage planes that are to be connected to PTHs for capacitance measurements are placed as close as possible to the dielectric layers that are being tested for anticipated changes of interest. Typically, this will include layers near the middle of the lay-up. Two voltage planes that are connected to the capacitance measuring PTHs typically flank each of the dielectric layers that are being focused on. The layers that are typically most sensitive to reflow-induced damage (mainly cracking in module areas) are those layers that are closer to the center of the stack-up. The ability of the present invention to focus on these "center of the stack-up layers" is a significant advantage over test structures that do not facilitate capacitance measurements between individual planes of the PCB stack-up (such as the test structure disclosed in the O'Toole article, discussed above in the "Background Art" Section).

Figure 5:
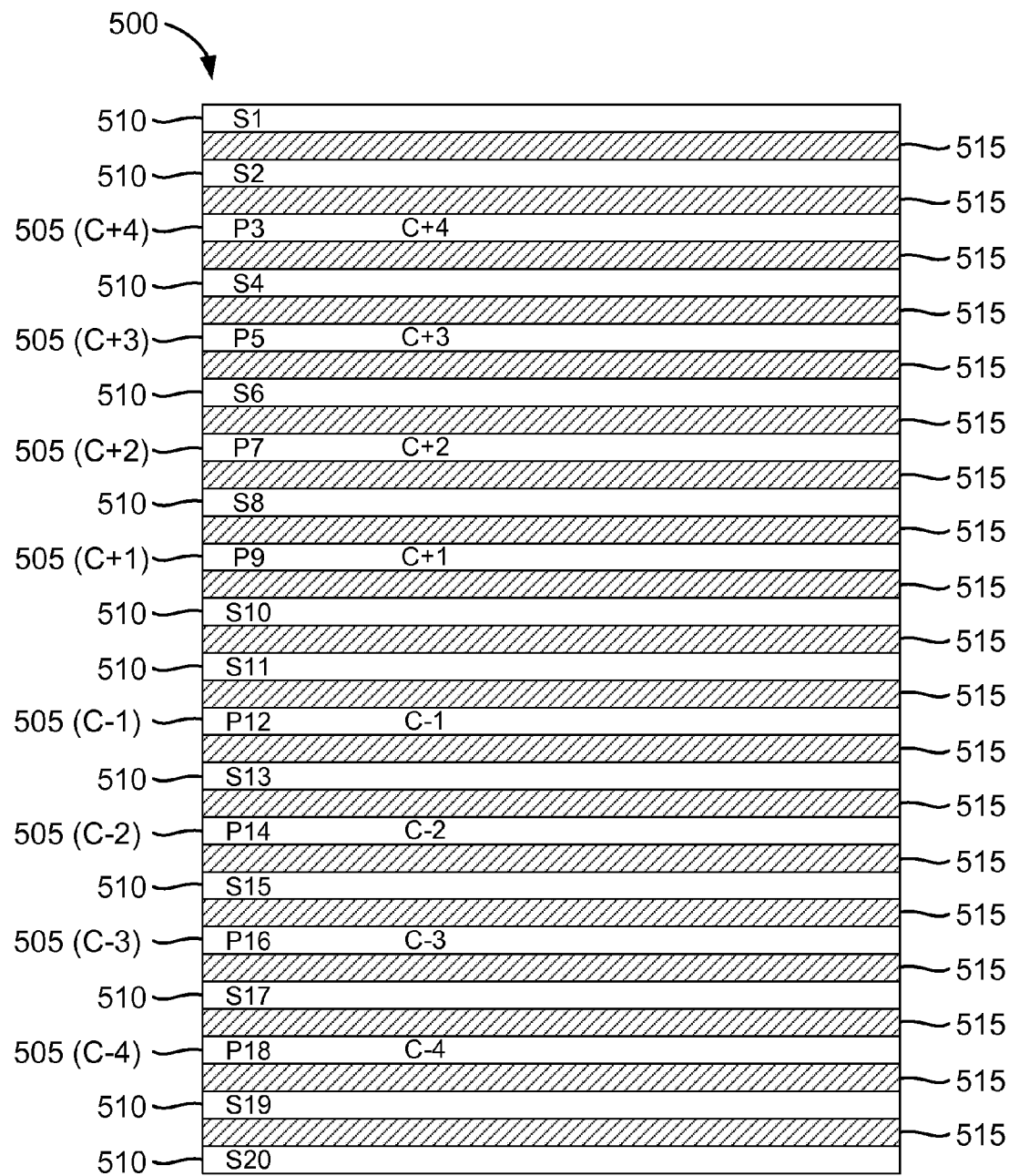
FIG. 5 is a cross-sectional view illustrating an exemplary laminate stack-up of the exemplary coupon layout shown in FIG. 4.

FIG. 5 is a cross-sectional view illustrating an exemplary laminate stack-up 500 of the exemplary coupon layout 400 shown in FIG. 4. The exemplary laminate stack-up 500 illustrated in FIG. 5 is used for each of the coupons 405 and 410 shown in FIG. 4.

The particular laminate stack-up illustrated in FIG. 5 is merely one example of a suitable coupon laminate stack-up and is not intended to limit the present invention. One skilled in the art will appreciate that any suitable laminate stack-up may be used in accordance with the preferred embodiments of the present invention in lieu of the exemplary laminate stack-up 500 illustrated in FIG. 5.

As illustrated in FIG. 5, the exemplary laminate stack-up 500 includes twenty electrically conductive planes (i.e., eight voltage planes 505 and twelve signal planes 510) each separated by one or more layers 515 of dielectric material. The electrically conductive planes typically comprise copper, but may be any suitable electrically conductive material. The voltage planes 505 are typically power planes or ground planes. Typically, the one or more layers 515 of dielectric material comprise one or more sheets of prepreg or laminate, but may be any suitable electrically nonconductive material.

The eight voltage planes 505 are also denoted in FIG. 5 as "P3", "P5", "P7", "P9", "P12", "P14", "P16", and "P18". The twelve signal planes 510 are also denoted in FIG. 5 as "S1", "S2", "S4", "S6", "S8", "S10", "S11", "S13", "S15", "S17", "S19", and "S20".

FIG. 5 further denotes which of the voltage planes 505 are connected to which of the PTHs 430. For the sake of clarity, the actual connections are not shown in FIG. 5. These connections, which are conventional, are identical for each of the coupons 405 and 410 shown in FIG. 4.

The voltage plane 505 denoted as "P3" in FIG. 5 is further denoted therein as "C+4, REF (I+4)" to indicate that this voltage plane layer is connected to the PTH 430 denoted with the marking "C+4" in FIG. 4.

The voltage plane 505 denoted as "P5" in FIG. 5 is further denoted therein as "C+3, REF (I+3)" to indicate that this voltage plane layer is connected to the PTH 430 denoted with the marking "C+3" in FIG. 4.

The voltage plane 505 denoted as "P7" in FIG. 5 is further denoted therein as "C+2, REF (I+2)" to indicate that this voltage plane layer is connected to the PTH 430 denoted with the marking "C+2" in FIG. 4.

The voltage plane 505 denoted as "P9" in FIG. 5 is further denoted therein as "C+1, REF (I+1)" to indicate that this voltage plane layer is connected to the PTH 430 denoted with the marking "C+1" in FIG. 4.

The voltage plane 505 denoted as "P12" in FIG. 5 is further denoted therein as "C−1, REF (I−1)" to indicate that this voltage plane layer is connected to the PTH 430 denoted with the marking "C−1" in FIG. 4.

The voltage plane 505 denoted as "P14" in FIG. 5 is further denoted therein as "C−2, REF (I−2)" to indicate that this voltage plane layer is connected to the PTH 430 denoted with the marking "C−2" in FIG. 4.

The voltage plane 505 denoted as "P16" in FIG. 5 is further denoted therein as "C−3, REF (I−3)" to indicate that this voltage plane layer is connected to the PTH 430 denoted with the marking "C−3" in FIG. 4.

The voltage plane 505 denoted as "P18" in FIG. 5 is further denoted therein as "C−4, REF (I−4)" to indicate that this voltage plane layer is connected to the PTH 430 denoted with the marking "C−4" in FIG. 4.

Seven dielectric capacitance measurements (i.e., in different regions of the laminate stack-up) may be acquired for each of the coupons 405 and 410 (shown in FIG. 4) by placing two probes on the PTHs 430 (shown in FIG. 4) that are adjacent to each other. A first capacitance measurement (i.e., the dielectric material between the voltage planes 505 denoted as "P9" and "P12" in FIG. 5) can be acquired by placing one probe on the PTH 430 denoted with the marking "C+1" in FIG. 4 and the other probe on the PTH 430 denoted with the marking "C−1" in FIG. 4. In this case, three layers 515 of dielectric material (as well as the signal planes 510 denoted as "S10" and "S11" in FIG. 5) lie in the capacitance measurement region between the voltage planes 505 denoted as "P9" and "P12" in FIG. 5.

A second capacitance measurement (i.e., the dielectric material between the voltage planes 505 denoted as "P3" and "P5" in FIG. 5) can be acquired by placing the probes on the PTHs 430 denoted with markings "C+4" and "C+3" in FIG. 4.

In this case, two of the layers 515 of dielectric material (as well as the signal plane 510 denoted as "S4" in FIG. 5) lie in the capacitance measurement region between the voltage planes 505 denoted as "P3" and "P5" in FIG. 5.

A third capacitance measurement (i.e., the dielectric material between the voltage planes 505 denoted as "P5" and "P7" in FIG. 5) can be acquired by placing the probes on the PTHs 430 denoted with markings "C+3" and "C+2" in FIG. 4. In this case, two of the layers 515 of dielectric material (as well as the signal plane 510 denoted as "S6" in FIG. 5) lie in the capacitance measurement region between the voltage planes 505 denoted as "P5" and "P7" in FIG. 5.

A fourth capacitance measurement (i.e., the dielectric material between the voltage planes 505 denoted as "P7" and "P9" in FIG. 5) can be acquired by placing the probes on the PTHs 430 denoted with markings "C+2" and "C+1" in FIG. 4. In this case, two of the layers 515 of dielectric material (as well as the signal plane 510 denoted as "S8" in FIG. 5) lie in the capacitance measurement region between the voltage planes 505 denoted as "P7" and "P9" in FIG. 5.

A fifth capacitance measurement (i.e., the dielectric material between the voltage planes 505 denoted as "P12" and "P14" in FIG. 5) can be acquired, by placing the probes on the PTHs 430 denoted with markings "C−1" and "C−2" in FIG. 4. In this case, two of the layers 515 of dielectric material (as well as the signal plane 510 denoted as "S13" in FIG. 5) lie in the capacitance measurement region between the voltage planes 505 denoted as "P12" and "P14" in FIG. 5.

A sixth capacitance measurement (i.e., the dielectric material between the voltage planes 505 denoted as "P14" and "P16" in FIG. 5) can be acquired by placing the probes on the PTHs 430 denoted with markings "C-2" and "C-3" in FIG. 4. In this case, two of the layers 515 of dielectric material (as well as the signal plane 510 denoted as "S15" in FIG. 5) lie in the capacitance measurement region between the voltage planes 505 denoted as "P14" and "P16" in FIG. 5.

A seventh capacitance measurement (i.e., the dielectric material between the voltage planes 505 denoted as "P16" and "P18" in FIG. 5) can be acquired, by placing the probes on the PTHs 430 denoted with markings "C−3" and "C−4" in FIG. 4. In this case, two of the layers 515 of dielectric material (as well as the signal plane 510 denoted as "S17" in FIG. 5) lie in the capacitance measurement region between the voltage planes 505 denoted as "P16" and "P18" in FIG. 5.

Generally, any number of the layers 515 of dielectric material and the signal planes 510 may lie within the capacitance measurement region. However, care should be exercised in the use of voltage planes that do not have connections to PTHs for capacitance measurement. For example, consider the case of a blank voltage plane that is between two voltage planes that are both connected to PTHs 430 for capacitance measurements. Any such capacitance measurements made between these two voltage planes may be more difficult to interpret due to the presence of the blank voltage plane between the two voltage planes.

Figure 6:
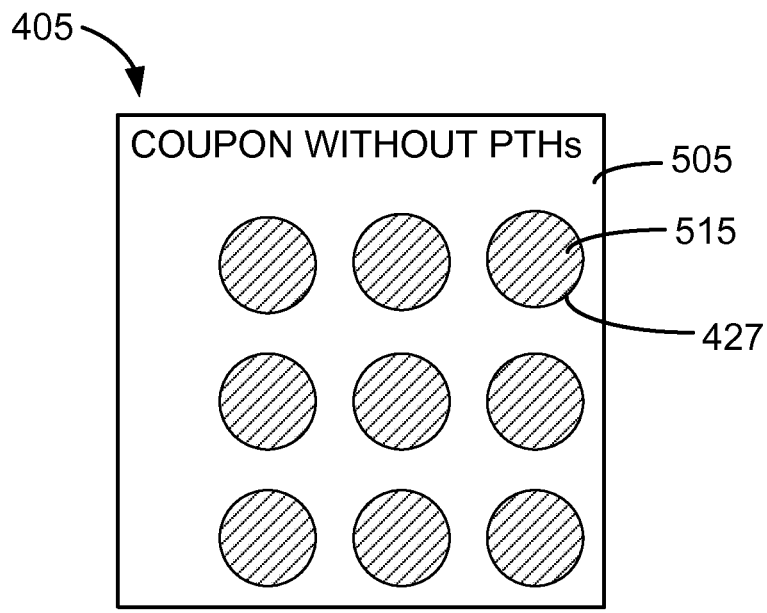
FIG. 6 is a top view illustrating a portion of a voltage plane layer shown in FIG. 5 in the coupon without plated through holes (PTHs) shown in FIG. 4.

FIG. 6 is a top view illustrating a portion of a voltage plane layer 505 shown in FIG. 5 in the coupon 405 without plated through holes (PTHs) shown in FIG. 4. Clearances 427 are etched in the voltage plane 505 to expose the underlying dielectric layer 515 where the PTHs of the 20×20 array would otherwise be located. That is, each of the clearances 427 in the coupon 405 without PTHs is provided in the same locations as each of the corresponding clearances 422 in the coupon 410 with PTHs (described below with reference to FIG. 7). Also, no holes are drilled in the clearances 427. Typically, a hole would be drilled in each such clearance to accommodate a PTH.

Figure 7:
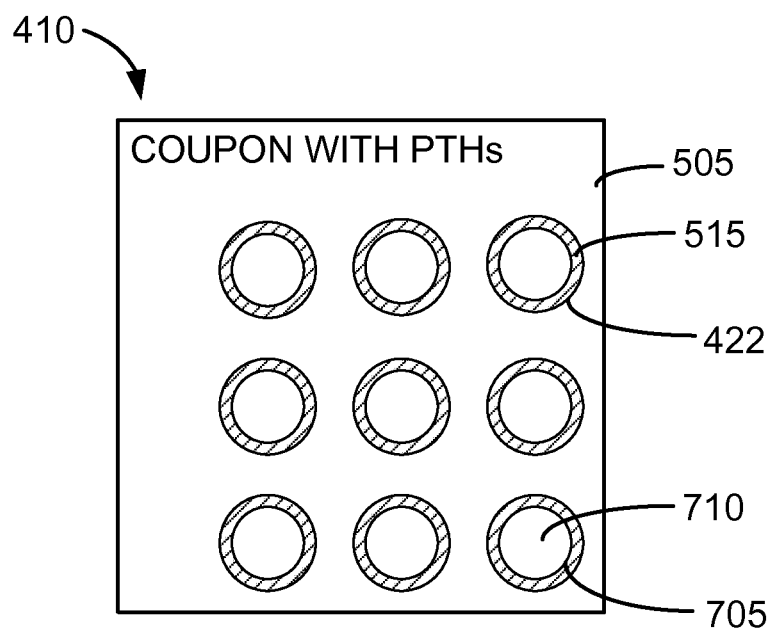
FIG. 7 is a top view illustrating a portion of a voltage plane layer shown in FIG. 5 in the coupon with plated through holes (PTHs) shown in FIG. 4.

FIG. 7 is a top view illustrating a portion of a voltage plane layer 505 shown in FIG. 5 in the coupon 410 with plated through holes (PTHs) shown in FIG. 4. Clearances 422 are etched in the voltage plane 505 to expose the underlying dielectric layer 515 where the PTHs of the 20×20 array are to be located. A hole 705 is then typically drilled through each of the clearances 422. Then a PTH 710 is formed in each of the holes 705.

As made clear in FIGS. 6 and 7, the number of the clearances 427 etched in the voltage plane 505 of the coupon 405 without PTHs is identical to the number of the clearances 422 etched in the voltage plane 505 of the coupon 410 with PTHs. The clearances 422 and 427 are identical in number, location and configuration.

Figure 8:
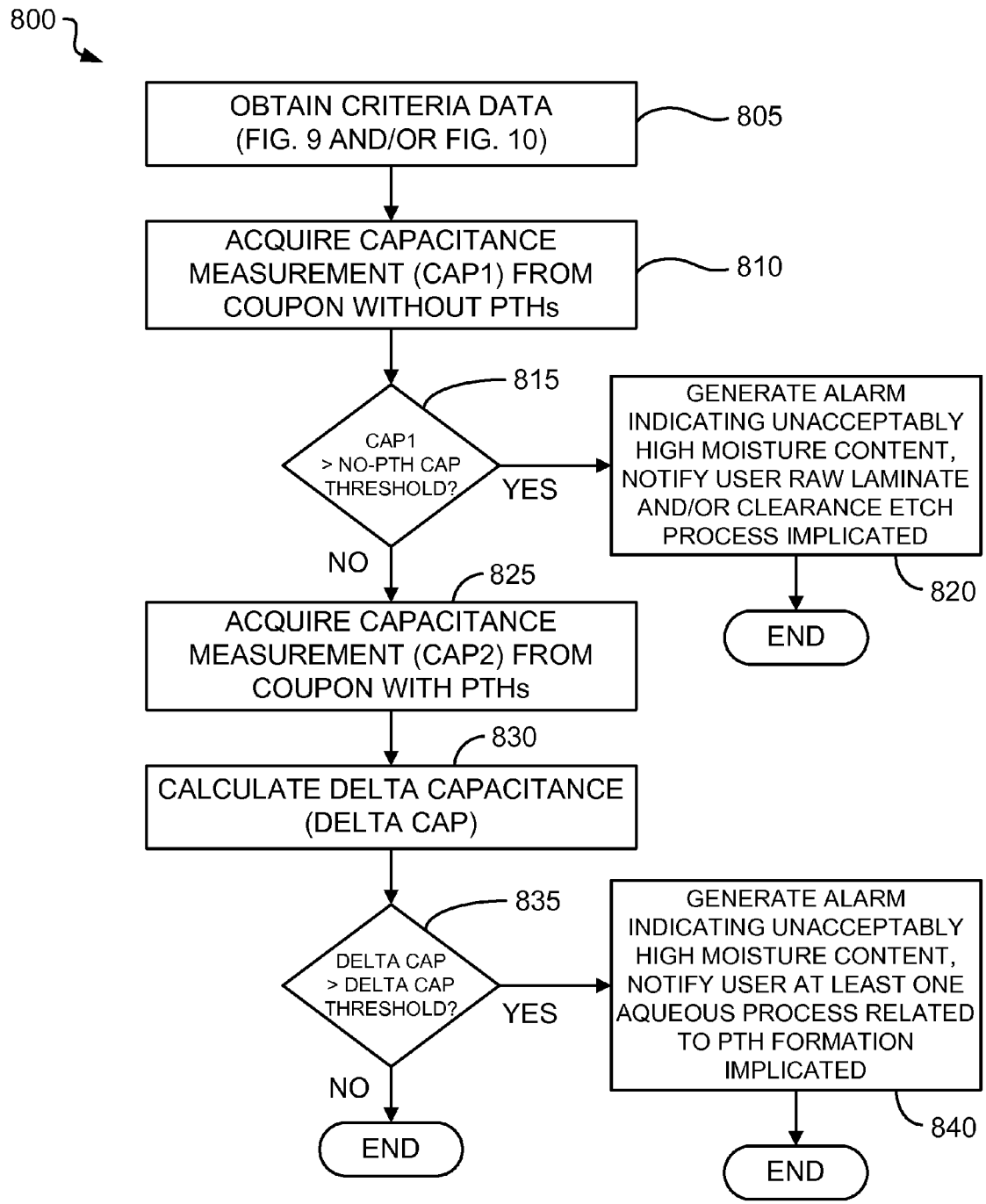
FIG. 8 is a flow diagram illustrating a method of determining moisture content in an electronic circuit board in accordance with the preferred embodiments of present invention.

FIG. 8 is a flow diagram illustrating a method 800 of determining moisture content in an electronic circuit board in accordance with the preferred embodiments of present invention. In the method 800, the steps discussed below (steps 805-840) are performed. These steps are set forth in their preferred order. It must be understood, however, that the various steps may occur simultaneously or at other times relative to one another. Moreover, those skilled in the art will appreciate that one or more steps may be omitted.

The method 800 begins with pass/fail criteria data being obtained (step 805). The criteria data (which are described in more detail below with reference to FIGS. 9 and 10) include one or more capacitance threshold values for each capacitance measurement region of the laminate stack-up of both types of coupons (i.e., coupons without PTHs and coupons with PTHs). Preferably, at least one of these capacitance threshold values is based on a comparison of a capacitance measurement made in a capacitance measurement region of a coupon with PTHs versus a capacitance measurement made in the same capacitance measurement region of a coupon without PTHs.

In accordance with the preferred embodiments of the present invention, the criteria data obtained in step 805 may include: a "no-PTH capacitance threshold" for each capacitance measurement region of coupons without PTHs; and a "delta capacitance threshold" for each capacitance measurement region of coupons with PTHs relative to coupons without PTHs. These preferred capacitance threshold values and their establishment are discussed below with reference to FIGS. 9 and 10.

The criteria data may be obtained during step 805 either by accessing previously established criteria data (e.g., criteria data that was previously established and stored in a database) or by performing the method 900 (which is described below with reference to FIG. 9) and/or the method 1000 (which is described below with reference to FIG. 10).

The method 800 continues by acquiring a capacitance measurement from a coupon without PTHs (step 810). This capacitance measurement is referred to as "CAP1" in FIG. 8. For example, a capacitance measurement may be acquired from a coupon without PTHs that has been removed from a PCB (e.g., the coupon 110 without PTHs that has been removed from the PCB 100 shown in FIG. 1) or a coupon without PTHs that has been removed from a panel (e.g., the coupon 220 without PTHs that has been removed from the panel 200 shown in FIG. 2). In accordance with the preferred embodiments of the present invention, the coupon without PTHs corresponds to the coupon 405 without PTHs shown in FIG. 4. Step 810 may be repeated for each capacitance measurement region of the coupon without PTHs.

In accordance with the preferred embodiments of the present invention, no reflow simulation has occurred with respect to the coupon without PTHs when the capacitance measurement(s) is/are acquired from the coupon in step 810. Likewise, in accordance with the preferred embodiments of the present invention, no reflow simulation has occurred with respect to the coupon with PTHs when its capacitance measurement(s) is/are acquired from the coupon in step 825 (described below). Avoiding the necessity of reflow simulation is a significant advantage of the present invention. The coupons are merely removed from the production part, and subsequently subjected to capacitance measurement.

Next, the method 800 determines if the capacitance measurement from the coupon without PTHs acquired in step 810 is larger than the "no-PTH capacitance threshold" (step 815). This threshold, which is referred to as "NO-PTH CAP THRESHOLD" in FIG. 8, is preferably one of the criteria data obtained in step 805. Step 815 may be omitted if a "no-PTH capacitance threshold" has not been established.

If the method 800 determines that the capacitance measurement from the coupon without PTHs acquired in step 810 is larger than the "no-PTH capacitance threshold" (step 815=Yes), then an alarm is generated indicating that unacceptably high moisture content has been detected (step 820). Detection of unacceptably high moisture content in the coupon without PTHs infers that the PCB or panel from which the coupon was removed likely also has unacceptably high moisture content. Preferably, the alarm notifies a user that a raw laminate used to fabricate the coupon without PTHs (as well as to fabricate the PCB or panel from which the coupon was removed) had unacceptably high moisture content "as delivered" and/or a clearance etch process used to produce the etched clearances in the raw laminate is/are implicated in the unacceptably high moisture content. The alarm may also identify specific items related to the raw laminate (e.g., manufacturer, storage parameters, and the like.) and the clearance etch process (e.g., aqueous bath parameters, bake cycle parameters, and the like) that the user should check.

In the embodiment illustrated in FIG. 8, the method ends after the alarm/notification of step 820. In an alternative embodiment, the method 800 continues after step 820 by returning to step 815 to determine if the capacitance measurement from any of other capacitance measurement regions of the coupon without PTHs is larger than the "no-PTH capacitance threshold". In another alternative embodiment, the method 800 continues after step 820 by advancing to step 825 (described below).

If the method 800 determines that the capacitance measurement from the coupon without PTHs acquired in step 810 is not larger than the "no-PTH capacitance threshold" (step 815=No), then the method 800 continues by acquiring a capacitance measurement from a coupon with PTHs (step 825). This capacitance measurement is referred to as "CAP2" in FIG. 8. For example, a capacitance measurement may be acquired from a coupon with PTHs that has been removed from a PCB (e.g., the coupon 115 with PTHs that has been removed from the PCB 100 shown in FIG. 1) or a coupon with PTHs that has been removed from a panel (e.g., the coupon 225 with PTHs that has been removed from the panel 200 shown in FIG. 2). In accordance with the preferred embodiments of the present invention, the coupon with PTHs corresponds to the coupon 410 with PTHs shown in FIG. 4. Step 825 may be repeated for each capacitance measurement region of the coupon with PTHs.

The method 800 then calculates a delta capacitance by subtracting the capacitance measurement acquired from the coupon without PTHs from the capacitance measurement acquired from the coupon with PTHs (step 830). The delta capacitance is referred to as "DELTA CAP" in FIG. 8. Step 830 may be repeated for each capacitance region of the coupons.

Next, the method 800 determines if the delta capacitance calculated in step 830 is larger than the "delta capacitance threshold" (step 835). This threshold, which is referred to as "DELTA CAP THRESHOLD" in FIG. 8, is one of the criteria data obtained in step 805.

If the method 800 determines that the delta capacitance calculated in step 830 is larger than the "delta capacitance threshold" (step 835=Yes), then an alarm is generated indicating that unacceptably high moisture content has been detected (step 840). Detection of unacceptably high moisture content infers that the PCB or panel from which the coupons were removed likely also has unacceptably high moisture content. Preferably, the alarm notifies a user that at least one aqueous process related to the PTH formation is implicated in the unacceptably high moisture content. The alarm may also identify specific items related to the implicated aqueous processes that the user should check, e.g., aqueous bath parameters, bake cycle parameters, and the like.

In the embodiment illustrated in FIG. 8, the method ends after the alarm/notification of step 840. In an alternative embodiment, the method 800 continues after step 840 by returning to step 835 to determine if the delta capacitance calculated in step 830 for any of the other capacitance measurement regions is larger than the "delta capacitance threshold".

If the method 800 determines that the delta capacitance calculated in step 830 is not larger than the "delta capacitance threshold" (step 835=No), then the method 800 ends. In an alternative embodiment, the method continues after step 835 by repeating the above steps with respect to each of the other capacitance measurement regions of the coupons.

Figure 9:
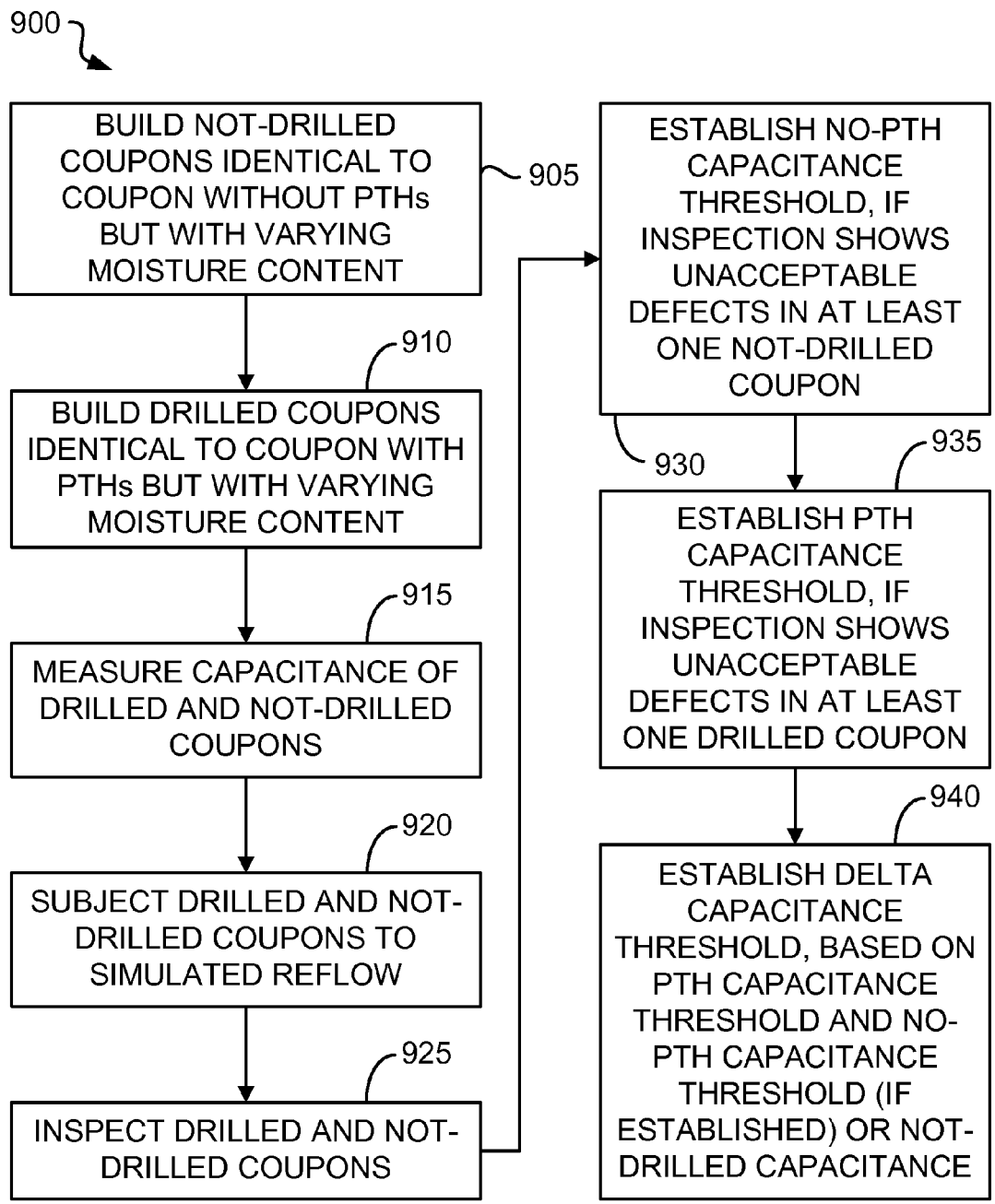
FIG. 9 is a flow diagram illustrating an exemplary method for performing the step of obtaining pass/fail criteria data in the method shown in FIG. 8.

FIG. 9 is a flow diagram illustrating an exemplary method for performing the step of obtaining pass/fail criteria data in the method 800 shown in FIG. 8. In the method 900, the steps discussed below (steps 905-940) are performed. These steps are set forth in their preferred order. It must be understood, however, that the various steps may occur simultaneously or at other times relative to one another. Moreover, those skilled in the art will appreciate that one or more steps may be omitted.

The method 900 begins with the fabrication of a plurality of coupons without PTHs (also referred to herein as "not-drilled coupons") identical to the coupon without PTHs in method 800 shown in FIG. 8 but with varying moisture content (step 905). These not-drilled coupons may be, for example, fabricated on one or more special PCB test panels (e.g., corresponding to the at least one coupon 310 without PTHs on the special PCB test panel 300 shown in FIG. 3). In accordance with the preferred embodiments of the present invention, each of these not-drilled coupons corresponds to the coupon 405 without PTHs shown in FIG. 4.

The method 900 continues with the fabrication of a plurality of coupons with PTHs (also referred to herein as "drilled coupons") identical to the coupon with PTHs in the method 800 shown in FIG. 8 but with varying moisture content (step 910). These drilled coupons may be, for example, fabricated on one or more special PCB test panel (e.g., corresponding to the at least one coupon 315 with PTHs on the special PCB test panel 300 shown in FIG. 3). In accordance with the preferred embodiments of the present invention, each of these drilled coupons corresponds to the coupon 410 with PTHs shown in FIG. 4.

The varying moisture content of the not-drilled coupons in step 905 and the drilled coupons in step 910 may be achieved by using materials and manufacturing processes that are within (or just beyond) "defined process limits" that are predicted to influence coupon water content. The terminology "defined process limits" refers to the process limits that define the materials and manufacturing processes for the fabrication of the actual production parts (e.g., the PCB 100 shown in FIG. 1 or the panel 200 shown in FIG. 2) on which the coupons in the method 800 shown in FIG. 8 are fabricated.

Next, the method 900 continues by measuring the capacitance of the drilled and not-drilled coupons (step 915). Step 915 may be repeated for each capacitance measurement region of the not-drilled and drilled coupons.

The method 900 then continues by subjecting the drilled and not-drilled coupons to simulated reflow (step 920). Each coupon is subjected to reflow conditions that simulate the process that the actual production parts (e.g., the PCB 100 shown in FIG. 1 or the panel 200 shown in FIG. 2) will experience. For example, the production parts may be subjected to five passes through a reflow profile that has a peak temperature of 245 C.

Next, the method 900 continues with the inspection of the drilled and not-drilled coupons for internal and/or external damage (step 925). For example, the coupons may be cross sectioned and inspected for internal defects (e.g., laminate crack, inner layer separation, and the like) and for external defects (e.g., blisters).

The method 900 then continues by establishing a "no-PTH capacitance threshold" for each capacitance measurement region, if possible (step 930). The "no-PTH capacitance threshold" is established in step 930 only if the inspection in step 925 shows unacceptable defects in at least one not-drilled coupon. The lowest capacitance corresponding to the first signs of unacceptable defects defines the highest allowed capacitance (i.e., the "no-PTH capacitance threshold") for each capacitance measurement region of the not-drilled coupons. In the event no defects are observed in the not-drilled coupons, even for the coupons that are predicted to have the highest water content, the method 1000 (which is described below with reference to FIG. 10) may be used to establish this piece of the criteria data.

Next, the method 900 continues by establishing a "PTH capacitance threshold" for each capacitance measurement region, if possible (step 935). The "PTH capacitance threshold" is established in step 935 only if the inspection in step 925 shows unacceptable defects in at least one drilled coupon. The lowest capacitance corresponding to the first signs of unacceptable defects defines the highest allowed capacitance (i.e., the "PTH capacitance threshold") for each capacitance measurement region of the drilled coupons. In the event no defects are observed in the drilled coupons, even for the coupons that are predicted to have the highest water content, the method 1000 (which is described below with reference to FIG. 10) may be used to establish this piece of the criteria data.

It is possible that the method 900 will lead to the establishment of the "PTH capacitance threshold" in step 935, but not the "no-PTH capacitance threshold" in step 930.

Then, the method 900 continues by establishing a "delta capacitance threshold" for each capacitance measurement region, if possible (step 940). For example, the "delta capacitance threshold" may be calculated as the difference between the "PTH capacitance threshold" and the "no-PTH capacitance threshold". Alternatively, the "delta capacitance threshold" may be calculated as the difference between the "PTH capacitance threshold" and a statistically derived (e.g., the average or mean) capacitance value measured in the step 915 with respect to the not-drilled coupons.

Figure 10:
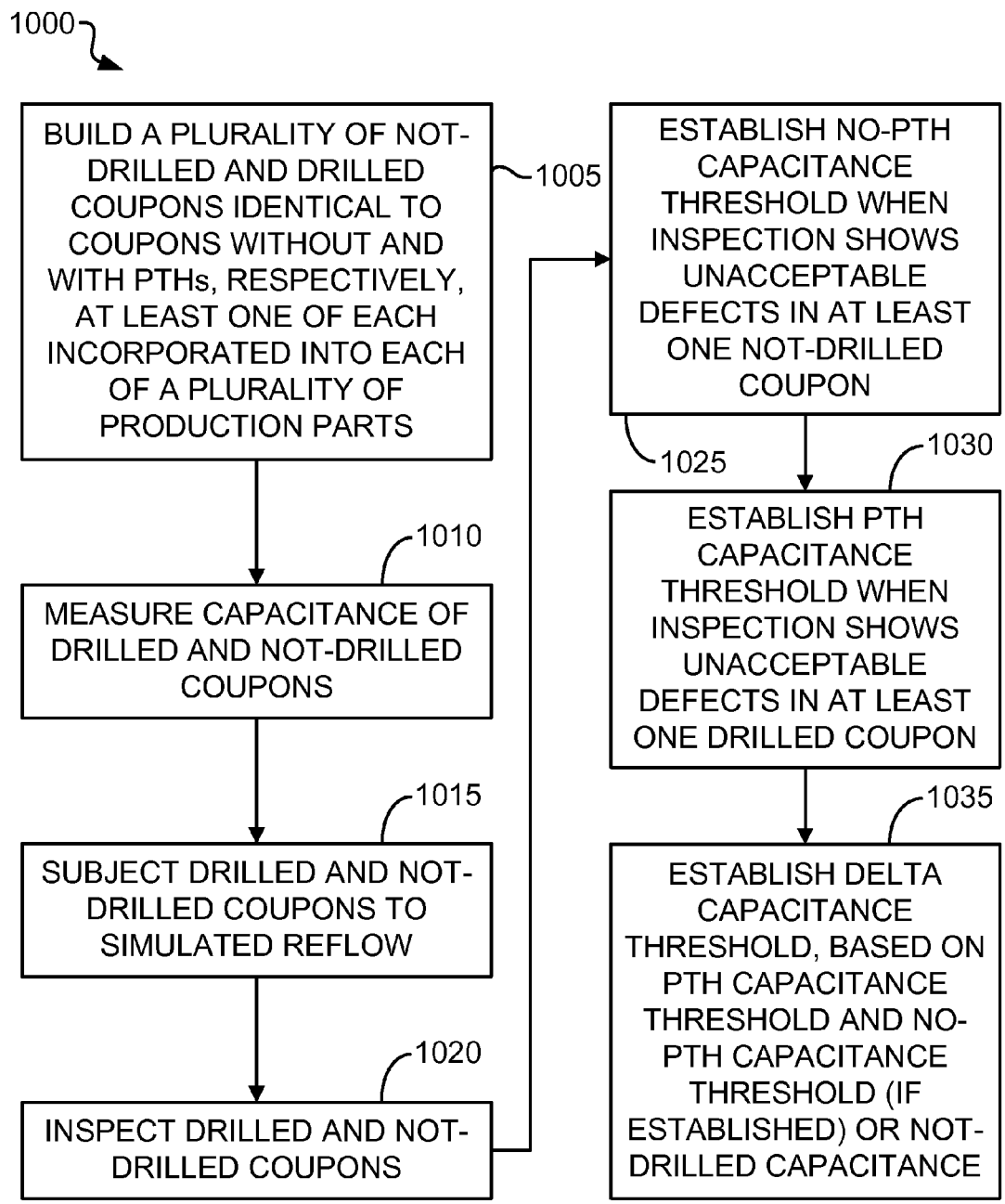
FIG. 10 is a flow diagram illustrating another exemplary method for performing the step of obtaining pass/fail criteria data in the method shown in FIG. 8.

FIG. 10 is a flow diagram illustrating another exemplary method for performing step of obtaining pass/fail criteria data in the method shown in FIG. 8. In the method 1000, the steps discussed below (steps 1005-1035) are performed. These steps are set forth in their preferred order. It must be understood, however, that the various steps may occur simultaneously or at other times relative to one another. Moreover, those skilled in the art will appreciate that one or more steps may be omitted.

The method 1000 relies on the actual variations in materials and manufacturing processes as the causes of variations in water content in actual production parts (e.g., the PCB 100 shown in FIG. 1 or the panel 200 shown in FIG. 2). Typically, the method 1000 will be used if the method 900 shown in FIG. 9 fails to establish criteria data, to refine criteria data established using the method 900 shown in FIG. 9, or if preferred by the user (i.e., the criteria data established using the method 1000 are more representative of actual production parts).

The method 1000 begins with the fabrication of a plurality of actual production parts each incorporating at least one coupon without PTHs (also referred to herein as "not-drilled coupons") and at least one coupon with PTHs (also referred to herein as "drilled coupons") identical to the coupon without PTHs and the coupon with PTHs in method 800 shown in FIG. 8 (step 1005). These drilled and not-drilled coupons may be, for example, fabricated on PCBs (e.g., corresponding to the coupons 110 and 115 on the PCB 100 shown in FIG. 1) or a panel (e.g., corresponding to the coupons 220 and 225 on the panel 200 shown in FIG. 2). In accordance with the preferred embodiments of the present invention, these drilled and not-drilled coupons correspond to the coupons 405 and 410 shown in FIG. 4.

Next, the method 1000 continues by measuring the capacitance of the drilled and not-drilled coupons (step 1010). Step 1010 may be repeated for each capacitance measurement region of the not-drilled and drilled coupons.

The method 1000 then continues by subjecting the drilled and not-drilled coupons to simulated reflow (step 1015). Each coupon is subjected to reflow conditions that simulate the process that the actual production parts (e.g., the PCB 100 shown in FIG. 1 or the panel 200 shown in FIG. 2) will experience. For example, the production parts may be subjected to five passes through a reflow profile that has a peak temperature of 245 C.

Next, the method 1000 continues with the inspection of the drilled and not-drilled coupons for internal and/or external damage (step 1020). For example, the coupons may be cross sectioned and inspected for internal defects (e.g., laminate crack, inner layer separation, and the like) and for external defects (e.g., blisters).

The method 1000 then continues by establishing a "no-PTH capacitance threshold" for each capacitance measurement region (step 1025). The "no-PTH capacitance threshold" is established in step 1025 when the inspection in step 1020 shows unacceptable defects in at least one not-drilled coupon. The lowest capacitance corresponding to the first signs of unacceptable defects defines the highest allowed capacitance (i.e., the "no-PTH capacitance threshold") for each capacitance measurement region of the not-drilled coupons.

Next, the method 1000 continues by establishing a "PTH capacitance threshold" for each capacitance measurement region (step 1030). The "PTH capacitance threshold" is established in step 1030 when the inspection in step 1020 shows unacceptable defects in at least one drilled coupon. The lowest capacitance corresponding to the first signs of unacceptable defects defines the highest allowed capacitance (i.e., the "PTH capacitance threshold") for each capacitance measurement region of the drilled coupons.

Then, the method 1000 continues by establishing a "delta capacitance threshold" for each capacitance measurement region (step 1035). For example, the "delta capacitance threshold" may be calculated as the difference between the "PTH capacitance threshold" and the "no-PTH capacitance threshold". Alternatively, the "delta capacitance threshold" may be calculated as the difference between the "PTH capacitance threshold" and a statistically derived (e.g., the average or mean) capacitance value measured in the step 1010 with respect to the not-drilled coupons.

As mentioned above, the method 1000 is more representative of actual production parts. Nonetheless, the use of the method 1000 as the first definition of the criteria data can be more costly than the method 900 shown in FIG. 9. This is because the production parts from which failed coupons were taken in the method 1000 may need to be scrapped. Hence, it is typically more desirable to use the method 900 shown in FIG. 9 to establish initial criteria that may be refined by the subsequent use of the method 1000.

Figure 11:
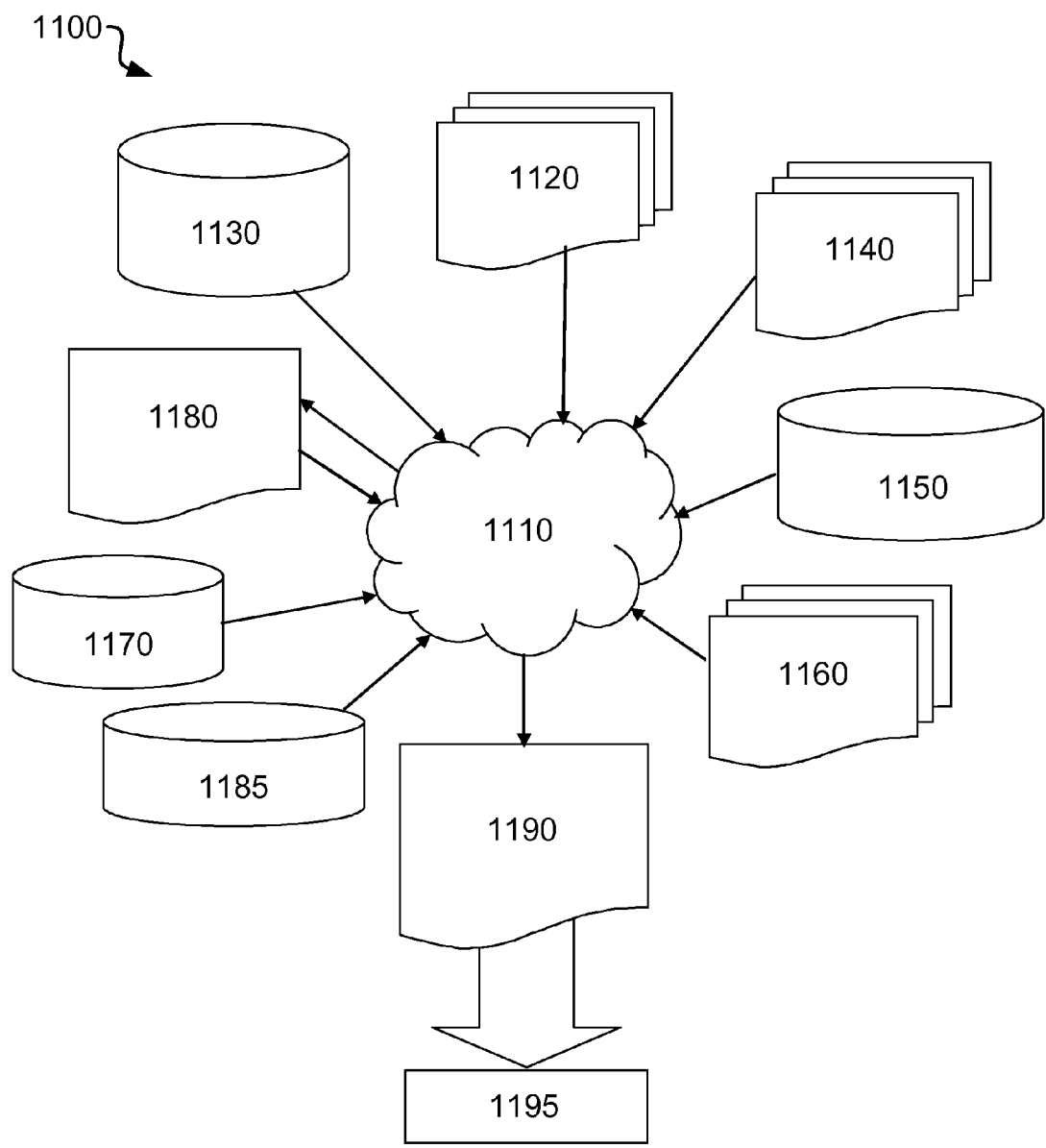
FIG. 11 is a flow diagram illustrating a design process used in electronic circuit board or semiconductor design, manufacture, and/or test in accordance with the preferred embodiments of present invention.

FIG. 11 shows a block diagram of an exemplary design flow 1100 used for example, in electronic circuit board or semiconductor IC logic design, simulation, test, layout, and manufacture. Design flow 1100 includes processes, machines and/or mechanisms for processing design structures or devices to generate logically or otherwise functionally equivalent representations of the design structures and/or devices described above and shown in FIGS. 1-3. The design structures processed and/or generated by design flow 1100 may be encoded on machine-readable transmission or storage media to include data and/or instructions that when executed or otherwise processed on a data processing system generate a logically, structurally, mechanically, or otherwise functionally equivalent representation of hardware components, circuits, devices, or systems. Machines include, but are not limited to, any machine used in an electronic circuit board or IC design process, such as designing, manufacturing, or simulating a circuit, component, device, or system. For example, machines may include: lithography machines, machines and/or equipment for generating masks (e.g. e-beam writers), computers or equipment for simulating design structures, any apparatus used in the manufacturing or test process, or any machines for programming functionally equivalent representations of the design structures into any medium (e.g. a machine for programming a programmable gate array).

Design flow 1100 may vary depending on the type of representation being designed. For example, a design flow 1100 for building an application specific IC (ASIC) may differ from a design flow 1100 for designing a standard component or from a design flow 1100 for instantiating the design into a programmable array, for example a programmable gate array (PGA) or a field programmable gate array (FPGA) offered by Altera® Inc. or Xilinx® Inc.

FIG. 11 illustrates multiple such design structures including an input design structure 1120 that is preferably processed by a design process 1110. Design structure 1120 may be a logical simulation design structure generated and processed by design process 1110 to produce a logically equivalent functional representation of a hardware device. Design structure 1120 may also or alternatively comprise data and/or program instructions that when processed by design process 1110, generate a functional representation of the physical structure of a hardware device. Whether representing functional and/or structural design features, design structure 1120 may be generated using electronic computer-aided design (ECAD) such as implemented by a core developer/designer. When encoded on a machine-readable data transmission, gate array, or storage medium, design structure 1120 may be accessed and processed by one or more hardware and/or software modules within design process 1110 to simulate or otherwise functionally represent an electronic component, circuit, electronic or logic module, apparatus, device, or system such as those shown in FIGS. 1-3. As such, design structure 1120 may comprise files or other data structures including human and/or machine-readable source code, compiled structures, and computer-executable code structures that when processed by a design or simulation data processing system, functionally simulate or otherwise represent circuits or other levels of hardware logic design. Such data structures may include hardware-description language (HDL) design entities or other data structures conforming to and/or compatible with lower-level HDL design languages such as Verilog and VHDL, and/or higher level design languages such as C or C++.

Design process 1110 preferably employs and incorporates hardware and/or software modules for synthesizing, translating, or otherwise processing a design/simulation functional equivalent of the components, circuits, devices, or logic structures shown in FIGS. 1-3 to generate a netlist 1180 which may contain design structures such as design structure 1120. Netlist 1180 may comprise, for example, compiled or otherwise processed data structures representing a list of wires, discrete components, logic gates, control circuits, I/O devices, models, etc. that describes the connections to other elements and circuits in an electronic circuit board or integrated circuit design. Netlist 1180 may be synthesized using an iterative process in which netlist 1180 is resynthesized one or more times depending on design specifications and parameters for the device. As with other design structure types described herein, netlist 1180 may be recorded on a machine-readable data storage medium or programmed into a programmable gate array. The medium may be a non-volatile storage medium such as a magnetic or optical disk drive, a programmable gate array, a compact flash, or other flash memory. Additionally, or in the alternative, the medium may be a system or cache memory, buffer space, or electrically or optically conductive devices and materials on which data packets may be transmitted and intermediately stored via the Internet, or other networking suitable means.

Design process 1110 may include hardware and software modules for processing a variety of input data structure types including netlist 1180. Such data structure types may reside, for example, within library elements 1130 and include a set of commonly used elements, circuits, and devices, including models, layouts, and symbolic representations, for a given manufacturing technology (e.g., different technology nodes, 32 nm, 45 nm, 90 nm, and the like). The data structure types may further include design specifications 1140, characterization data 1150, verification data 1160, design rules 1170, and test data files 1185 which may include input test patterns, output test results, and other testing information. Design process 1110 may further include, for example, standard mechanical design processes such as stress analysis, thermal analysis, mechanical event simulation, process simulation for operations such as casting, molding, die press forming, and the like. One of ordinary skill in the art of mechanical design can appreciate the extent of possible mechanical design tools and applications used in design process 1110 without deviating from the scope and spirit of the invention. Design process 1110 may also include modules for performing standard circuit design processes such as timing analysis, verification, design rule checking, place and route operations, and the like.

Design process 1110 employs and incorporates logic and physical design tools such as HDL compilers and simulation model build tools to process design structure 1120 together with some or all of the depicted supporting data structures along with any additional mechanical design or data (if applicable), to generate a second design structure 1190. Design structure 1190 resides on a storage medium or programmable gate array in a data format used for the exchange of data of mechanical devices and structures (e.g. information stored in a IGES, DXF, Parasolid XT, JT, DRG, or any other suitable format for storing or rendering such mechanical design structures). Similar to design structure 1120, design structure 1190 preferably comprises one or more files, data structures, or other computer-encoded data or instructions that reside on transmission or data storage media and that when processed by an ECAD system generate a logically or otherwise functionally equivalent form of one or more of the embodiments of the invention shown in FIGS. 1-3. In one embodiment, design structure 1190 may comprise a compiled, executable HDL simulation model that functionally simulates the devices shown in FIG. 1-10.

Design structure 1190 may also employ a data format used for the exchange of layout data of integrated circuits and/or symbolic data format (e.g. information stored in a GDSII (GDS2), GL1, OASIS, map files, or any other suitable format for storing such design data structures). Design structure 1190 may comprise information such as, for example, symbolic data, map files, test data files, design content files, manufacturing data, layout parameters, wires, levels of metal, vias, shapes, data for routing through the manufacturing line, and any other data required by a manufacturer or other designer/developer to produce a device or structure as described above and shown in FIGS. 1-3. Design structure 1190 may then proceed to a stage 1195 where, for example, design structure 1190: proceeds to tape-out, is released to manufacturing, is released to a mask house, is sent to another design house, is sent back to the customer, and the like.

One skilled in the art will appreciate that many variations are possible within the scope of the present invention. Thus, while the present invention has been particularly shown and described with reference to the preferred embodiments thereof, it will be understood by those skilled in the art that these and other changes in form and detail may be made therein without departing from the spirit and scope of the present invention.

What is claimed is:

1. An electronic circuit board, comprising:
    a first coupon having a laminate stack-up that includes voltage planes separated from each other by a dielectric material, wherein each of the voltage planes includes a plurality of etched clearances with neither vias nor drilled holes extending therethrough;
    a second coupon substantially identical to the first coupon except that each of the voltage planes of the second coupon includes a plurality of etched clearances corresponding to the etched clearances of the first coupon but with plated through holes (PTHs) extending therethrough.

2. The electronic circuit board as recited in claim 1, wherein the electronic circuit board is a printed circuit board (PCB) that incorporates the first and second coupons, wherein the PCB has a laminate stack-up that is identical to that of the first and second coupons, wherein the first and second coupons are removable from the PCB, and wherein the first and second coupons include at least one coupon design feature that reflects at least one feature of the PCB that is known or predicted to be associated with solder reflow-induced damage to the laminate of the PCB within or near the at least one PCB feature.

3. The electronic circuit board as recited in claim 1, wherein the electronic circuit board is a panel that incorporates one or more printed circuit boards (PCBs) and the first and second coupons in separate areas of the panel, wherein each of the PCBs in the panel has a laminate stack-up that is identical to that of the first and second coupons, wherein the first and second coupons are removable from the panel, and wherein the first and second coupons include at least one coupon design feature that reflects at least one feature of one or more of the PCBs that is/are known or predicted to be associated with solder reflow-induced damage to the laminate of the PCB within or near the at least one PCB feature.

4. The electronic circuit board as recited in claim 1, wherein the electronic circuit board is a special printed circuit board (PCB) test panel that incorporates the first and second coupons, and wherein the first and second coupons include at least one coupon design feature that reflects at least one feature of a production PCB that is known or predicted to be associated with solder reflow-induced damage to the laminate of the production PCB within or near the at least one production PCB feature.

5. The electronic circuit board as recited in claim 2, wherein the at least one coupon design feature is selected from a group consisting of via-to-via pitch, drilled via diameter, drilled via clearance diameter, array size, and combinations thereof.

6. The electronic circuit board as recited in claim 5, wherein the PCB includes a module site and the at least one PCB feature is within or near the module site, and wherein the first and second coupons are present on the PCB near the module site.

7. The electronic circuit board as recited in claim 3, wherein the at least one coupon design feature is selected from a group consisting of via-to-via pitch, drilled via diameter, drilled via clearance diameter, array size, and combinations thereof.

8. The electronic circuit board as recited in claim 7, wherein each of the one or more PCBs includes a module site and the at least one PCB feature is within or near the module site.

9. The electronic circuit board as recited in claim 4, wherein the at least one coupon design feature is selected from a group consisting of via-to-via pitch, drilled via diameter, drilled via clearance diameter, array size, and combinations thereof.

10. The electronic circuit board as recited in claim 9, wherein the production PCB includes a module site and the at least one production PCB feature is within or near the module site.

11. A method of determining moisture content in an electronic circuit board, wherein the electronic circuit board includes a first coupon and a second coupon, comprising the steps of:
    obtaining criteria data;
    acquiring a capacitance measurement from the first coupon, wherein the first coupon has a laminate stack-up that includes voltage planes separated from each other by a dielectric material, wherein each of the voltage planes includes a plurality of etched clearances with neither vias nor drilled holes extending therethrough, and wherein the capacitance measurement acquired from the first coupon is measured between the voltage planes;

acquiring a capacitance measurement from the second coupon, wherein the second coupon is substantially identical to the first coupon except that each of the voltage planes of the second coupon includes a plurality of etched clearances corresponding to the etched clearances of the first coupon but with plated through holes (PTHs) extending therethrough, and wherein the capacitance measurement acquired from the second coupon is measured between the voltage planes;

calculating a delta capacitance by subtracting the capacitance measurement acquired from the first coupon from the capacitance measurement acquired from the second coupon;

comparing the delta capacitance to a delta capacitance threshold from the criteria data;

if the delta capacitance is greater than the delta capacitance threshold, then generating an alarm indicating unacceptably high moisture content.

12. The method as recited in claim 11, wherein the alarm notifies a user that at least one aqueous process related to PTH formation is implicated in the unacceptably high moisture content.

13. The method as recited in claim 11, further comprising the steps of:

comparing the capacitance measurement of the first coupon to a no-PTH capacitance threshold;

if the capacitance measurement from the first coupon is greater than the no-PTH capacitance threshold, then generating a secondary alarm indicating unacceptably high moisture content.

14. The method as recited in claim 13, wherein the secondary alarm notifies a user that a raw laminate used to fabricate the first coupon had unacceptably high moisture content "as delivered" and/or a clearance etch process used to produce the etched clearances in the raw laminate is/are implicated in the unacceptably high moisture content.

15. The method as recited in claim 11, wherein the step of obtaining criteria data includes the steps of:

building a plurality of not-drilled coupons identical to the first coupon but with varying moisture content;

building a plurality of drilled coupons identical to the second coupon but with varying moisture content;

measuring the capacitance of the drilled and not-drilled coupons;

subjecting the drilled and not-drilled coupons to simulated reflow;

inspecting the drilled and not-drilled coupons for internal and/or external damage after subjecting the drilled and not-drilled coupons to simulated reflow;

establishing a PTH capacitance threshold based on the inspecting step with respect to the plurality of drilled coupons and the capacitance value measured in the measuring step corresponding to one or more of the plurality of drilled coupons;

establishing the delta capacitance threshold based on the PTH capacitance threshold and the capacitance value measured in the measuring step corresponding to one or more of the plurality of not-drilled coupons.

16. The method as recited in claim 15, further comprising the step of:

establishing a no-PTH capacitance threshold based on the inspecting step with respect to the plurality of not-drilled coupons and the capacitance values measured in the measuring step corresponding to one or more of the plurality of not-drilled coupons;

wherein the step of establishing the delta capacitance threshold is based on the PTH capacitance threshold and the no-PTH capacitance threshold.

17. The method as recited in claim 11, wherein the step of obtaining criteria data includes the steps of:

building a plurality of not-drilled and drilled coupons identical to the first and second coupons, respectively, wherein at least one of the not-drilled coupons and at least one of the drilled coupons is incorporated into each of a plurality of production parts;

measuring the capacitance of the drilled and not-drilled coupons;

subjecting the drilled and not-drilled coupons to simulated reflow;

inspecting the drilled and not-drilled coupons for internal and/or external damage after subjecting the drilled and not-drilled coupons to simulated reflow;

establishing a PTH capacitance threshold based on the inspecting step with respect to the plurality of drilled coupons and the capacitance value measured in the measuring step corresponding to one or more of the plurality of drilled coupons;

establishing the delta capacitance threshold based on the PTH capacitance threshold and the capacitance value measured in the measuring step corresponding to one or more of the plurality of not-drilled coupons.

18. The method as recited in claim 17, further comprising the step of:

establishing a no-PTH capacitance threshold based on the inspecting step with respect to the plurality of not-drilled coupons and the capacitance values measured in the measuring step corresponding to one or more of the plurality of not-drilled coupons;

wherein the step of establishing the delta capacitance threshold is based on the PTH capacitance threshold and the no-PTH capacitance threshold.

19. A design structure tangibly embodied in a non-transitory machine readable medium for designing, manufacturing, or testing an electronic circuit board and/or integrated circuit, the design structure comprising:

an electronic circuit board, comprising:

a first coupon having a laminate stack-up that includes voltage planes separated from each other by a dielectric material, wherein each of the voltage planes includes a plurality of etched clearances with neither vias nor drilled holes extending therethrough;

a second coupon substantially identical to the first coupon except that each of the voltage planes of the second coupon includes a plurality of etched clearances corresponding to the etched clearances of the first coupon but with plated through holes (PTHs) extending therethrough.

20. The design structure as recited in claim 19, wherein the electronic circuit board is a printed circuit board (PCB) that incorporates the first and second coupons, wherein the PCB has a laminate stack-up that is identical to that of the first and second coupons, wherein the first and second coupons are removable from the PCB, and wherein the first and second coupons include at least one coupon design feature that reflects at least one feature of the PCB that is known or predicted to be associated with solder reflow-induced damage to the laminate of the PCB within or near the at least one PCB feature.

21. The design structure as recited in claim 19, wherein the electronic circuit board is a panel that incorporates one or more printed circuit boards (PCBs) and the first and second coupons in separate areas of the panel, wherein each of the PCBs in the panel has a laminate stack-up that is identical to that of the first and second coupons, wherein the first and second coupons are removable from the panel, and wherein the first and second coupons include at least one coupon design feature that reflects at least one feature of one or more of the PCBs that is/are known or predicted to be associated with solder reflow-induced damage to the laminate of the PCB within or near the at least one PCB feature.

22. The design structure as recited in claim 19, wherein the electronic circuit board is a special printed circuit board (PCB) test panel that incorporates the first and second coupons, and wherein the first and second coupons include at least one coupon design feature that reflects at least one feature of a production PCB that is known or predicted to be associated with solder reflow-induced damage to the laminate of the production PCB within or near the at least one production PCB feature.

23. The design structure as recited in claim 19, wherein the design structure comprises a netlist.

24. The design structure as recited in claim 19, wherein design structure resides on storage medium as a data format used in the exchange of layout data of integrated circuits.

25. A design process tangibly embodied in a non-transitory machine readable medium for determining moisture content in an electronic circuit board, wherein the electronic circuit board includes a first coupon and a second coupon, the design process comprising the steps of:

obtaining criteria data;
acquiring a capacitance measurement from the first coupon, wherein the first coupon has a laminate stack-up that includes voltage planes separated from each other by a dielectric material, wherein each of the voltage planes includes a plurality of etched clearances with neither vias nor drilled holes extending therethrough, and wherein the capacitance measurement acquired from the first coupon is measured between the voltage planes;
acquiring a capacitance measurement from the second coupon, wherein the second coupon is substantially identical to the first coupon except that each of the voltage planes of the second coupon includes a plurality of etched clearances corresponding to the etched clearances of the first coupon but with plated through holes (PTHs) extending therethrough, and wherein the capacitance measurement acquired from the second coupon is measured between the voltage planes;
calculating a delta capacitance by subtracting the capacitance measurement acquired from the first coupon from the capacitance measurement acquired from the second coupon;
comparing the delta capacitance to a delta capacitance threshold from the criteria data;
if the delta capacitance is greater than the delta capacitance threshold, then generating an alarm indicating unacceptably high moisture content.

\* \* \* \* \*